US012667369B2

(12) United States Patent
Takahashi et al.

(10) Patent No.:  US 12,667,369 B2
(45) Date of Patent:       Jun. 30, 2026

(54) MEDICAL DEVICE AND TREATMENT METHOD

(71) Applicant: TERUMO KABUSHIKI KAISHA, Tokyo (JP)

(72) Inventors: Yusuke Takahashi, Kanagawa (JP); Yukitoshi Kato, Kanagawa (JP); Tomoaki Takemura, Kawasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 172 days.

(21) Appl. No.: 18/772,958

(22) Filed:     Jul. 15, 2024

(65)            Prior Publication Data

US 2024/0366231 A1     Nov. 7, 2024

Related U.S. Application Data

(60) Division of application No. 16/733,771, filed on Jan. 3, 2020, now Pat. No. 12,053,184, which is a
(Continued)

(30)        Foreign Application Priority Data

Jul. 4, 2017    (JP) ................................. 2017-131216

(51) Int. Cl.
*A61B 17/128*       (2006.01)
*A61B 17/00*        (2006.01)
*A61B 18/00*        (2006.01)

(52) U.S. Cl.
CPC .............................. *A61B 17/1285* (2013.01); *A61B 2017/00252* (2013.01); *A61B 2017/00367* (2013.01);
(Continued)

(58) Field of Classification Search
None
See application file for complete search history.

(56)            References Cited

U.S. PATENT DOCUMENTS 7,270,662 B2 *   9/2007  Visram .............. A61B 18/1492
                                                      606/41
8,939,970 B2 *   1/2015  Stone ................ A61B 18/1206
                                                      606/41
(Continued)

FOREIGN PATENT DOCUMENTS

CN         103768705 A      5/2014
CN         105555204 A      5/2016
(Continued)

OTHER PUBLICATIONS

International Search Report (PCT/ISA/210) mailed on Sep. 18, 2018, by the Japanese Patent Office as the International Searching Authority for International Application No. PCT/JP2018/025095.
(Continued)

*Primary Examiner* — Shaun L David
(74) *Attorney, Agent, or Firm* — Buchanan Ingersoll & Rooney PC

(57)            ABSTRACT

A medical device is disclosed, which is capable of preventing a maintenance treatment element imparting energy to biological tissue from being displaced from a treatment target site and a treatment method performed on a heart failure patient. A medical device is disclosed, which includes a shaft portion, an expandable and contractible expansion body provided on a distal side of the shaft portion, and a maintenance treatment element disposed in the expansion body and imparting energy to biological tissue. The expansion body includes a concave portion recessed in a direction intersecting with an axial direction of the shaft portion. The maintenance treatment element is disposed in the concave portion.

7 Claims, 21 Drawing Sheets

Related U.S. Application Data continuation of application No. PCT/JP2018/025095, filed on Jul. 2, 2018.

(52) U.S. Cl.
CPC .............. *A61B 2018/00214* (2013.01); *A61B 2018/00357* (2013.01)

(56)                  References Cited

U.S. PATENT DOCUMENTS

| | | | | |
|---|---|---|---|---|
| 8,979,839 | B2* | 3/2015 | De La Rama ..... | A61B 18/1492 606/41 |
| 9,579,149 | B2* | 2/2017 | Kelly ....................... | A61N 7/02 |
| 10,292,690 | B2* | 5/2019 | Celermajer ........ | A61B 17/0057 |
| 2004/0187875 | A1* | 9/2004 | He ..................... | A61B 18/1492 606/41 |
| 2004/0260277 | A1 | 12/2004 | Maguire | |
| 2005/0240147 | A1 | 10/2005 | Makower et al. | |
| 2007/0083194 | A1* | 4/2007 | Kunis ............... | A61B 18/1492 606/41 |
| 2007/0179426 | A1 | 8/2007 | Selden | |
| 2008/0033421 | A1* | 2/2008 | Davis ................ | A61B 17/0057 606/41 |
| 2008/0033425 | A1* | 2/2008 | Davis ................ | A61B 17/0057 606/41 |
| 2009/0326572 | A1 | 12/2009 | Peh et al. | |
| 2010/0094209 | A1 | 4/2010 | Drasler et al. | |
| 2012/0259263 | A1* | 10/2012 | Celermajer .... | A61B 17/320016 604/509 |
| 2013/0331920 | A1* | 12/2013 | Osypka ............... | A61N 1/0587 607/122 |
| 2014/0005660 | A1* | 1/2014 | Edwards .......... | A61M 16/0438 606/41 |
| 2014/0350565 | A1 | 11/2014 | Yacoby et al. | |
| 2016/0022970 | A1* | 1/2016 | Forcucci ............... | A61B 17/11 604/8 |
| 2016/0331459 | A1* | 11/2016 | Townley ............... | A61N 5/022 |
| 2016/0374682 | A1 | 12/2016 | Leonard et al. | |
| 2017/0151014 | A1* | 6/2017 | Perfler ............... | A61B 18/1492 |
| 2018/0177516 | A1* | 6/2018 | Vardi ..................... | A61B 34/73 |
| 2019/0069949 | A1* | 3/2019 | Vrba .............. | A61B 17/320068 |
| 2019/0069950 | A1* | 3/2019 | Viswanathan ..... | A61B 18/1492 |
| 2020/0138445 | A1 | 5/2020 | Takahashi et al. | |

FOREIGN PATENT DOCUMENTS

| | | |
|---|---|---|
| JP | 2012050538 A | 3/2012 |
| JP | 2012505050 A | 3/2012 |
| JP | 2013176504 A | 9/2013 |
| JP | 2017060825 A | 3/2017 |
| JP | 2017508581 A | 3/2017 |
| WO | 2014150106 A1 | 9/2014 |
| WO | 2017099950 A1 | 6/2017 |

OTHER PUBLICATIONS

Office Action (Notice of Reasons for Revocation) issued Dec. 19, 2022, by the Japan Patent Office in corresponding Japanese Patent Application No. 2019-527703 and an English translation of the Office Action. (10 pages).

Office Action (The First Office Action) issued Oct. 10, 2022, by the National Intellectual Property Administration, P. R. China in corresponding Chinese Patent Application No. 201880043317.X and an English Translation of the Office Action. (13 pages).

Written Opinion (PCT/ISA/237) mailed on Sep. 18, 2018, by the Japanese Patent Office as the International Searching Authority for International Application No. PCT/JP2018/025095.

The extended European Search Report issued Feb. 24, 2021, by the European Patent Office in corresponding European Patent Application No. 18827416.1-1113. (7 pages).

An English Translation of the International Search Report (Form PCT/ISA/210) and the Written Opinion of the International Searching Authority, (Form PCT/ISA/237) issued on Sep. 18, 2018, by the Japanese Patent Office in corresponding International Application No. PCT/JP2018/025095 (8 pages).

* cited by examiner

MEDICAL DEVICE AND TREATMENT METHOD

CROSS-REFERENCES TO RELATED APPLICATIONS

This application is a divisional of U.S. application Ser. No. 16/733,771 filed on Jan. 3, 2020, which is a continuation of International Application No. PCT/JP2018/025095 filed on Jul. 2, 2018, which claims priority to Japanese Application No. 2017-131216 filed on Jul. 4, 2017, the entire content of all three of which is incorporated herein by reference.

FIELD OF THE DISCLOSURE

The present disclosure generally relates to a medical device provided with a maintenance treatment element imparting energy to biological tissue and a treatment method performed on a heart failure patient.

BACKGROUND DISCUSSION

Chronic heart failure is known as a heart disease. Chronic heart failure can be broadly classified into systolic and diastolic dysfunctions based on cardiac function indicators. The myocardium of a patient suffering from diastolic dysfunction is enlarged, which results in an increase in stiffness (hardness), an increase in left atrial blood pressure, and a decline in the pump function of his or her heart. As a result, the patient can exhibit a heart failure symptom such as pulmonary edema.

Other heart diseases, for example, include the blood pressure on the right atrium side increasing due to pulmonary hypertension and a decline in the pump function of the heart arising to result in a heart failure symptom.

In recent years, shunt treatment for heart failure patients for forming a shunt (through-hole) in the atrial septum has attracted attention as a treatment method by which heart failure symptoms can be alleviated. The shunt serves as an escape route for an increased atrial pressure.

For example, during the shunt treatment described in Japanese Patent Application Publication No. 2017-60825 A, a medical instrument for shunt formation is delivered to the atrial septum by a transvenous approach and a shunt is formed in the atrial septum. Further, during the shunt treatment described above, treatment for denaturing biological tissue around the shunt is performed by means of, for example, an ablation catheter provided with an electrode (maintenance treatment element) so that the shunt is maintained at a desired size for a predetermined period after the shunt formation in the atrial septum.

It may become difficult to maintain the shunt at the desired size and a decline in therapeutic effect may arise when the electrode provided on the catheter is displaced during the ablation for the shunt treatment described above.

SUMMARY

A medical device is disclosed, which is capable of preventing a maintenance treatment element imparting energy to biological tissue from being displaced from a treatment target site and a treatment method performed on a heart failure patient.

A medical device according to the present disclosure includes a shaft portion, an expandable and contractible expansion body disposed distal of the shaft portion, and a maintenance treatment element disposed in the expansion body and performing a predetermined maintenance treatment on biological tissue. The expansion body includes a concave portion recessed in a direction intersecting with an axial direction of the shaft portion. The maintenance treatment element is disposed in the concave portion.

A treatment method according to the present disclosure includes an expansion process of expanding a through-hole formed in an atrial septum so as to allow a right atrium and a left atrium of a heart failure patient to communicate with each other, a confirmation process of confirming hemodynamics (i.e., dynamics of blood flow) in a vicinity of the through-hole, and a process of performing maintenance treatment for maintaining a size of the through-hole.

In accordance with an aspect, the medical device is capable of preventing the maintenance treatment element disposed in the concave portion from being displaced from a treatment target site by the concave portion formed when the expansion body is expanded to deform being disposed at the treatment target site (such as the edge portion of the through-hole formed in the atrial septum). As a result, a surgeon such as a doctor using the medical device can perform an appropriate treatment by means of the maintenance treatment element.

In accordance with another aspect, the treatment method includes the confirmation process of confirming the hemodynamics in the vicinity of the through-hole formed in the atrial septum. Accordingly, a surgeon such as a doctor can obtain a determination index during his or her procedure as to whether or not the through-hole formed in the atrial septum is formed in a desired size and can improve the therapeutic effect of heart failure treatment.

In accordance with an aspect, a medical device is disclosed comprising: a shaft portion; an expandable and contractible expansion body disposed distal of the shaft portion, the expansion body including a plurality of linear expansion portions disposed at different positions in a circumferential direction of the shaft portion, each of the plurality of linear expansion portions including a concave portion recessed in a direction intersecting with an axial direction of the shaft portion; and a maintenance treatment element disposed in each of the linear expansion portions and performing a predetermined maintenance treatment on biological tissue, and wherein the maintenance treatment element is disposed in the concave portion.

In accordance with another aspect, a treatment method is disclosed, the method comprising: expanding a through-hole formed in an atrial septum so as to allow a right atrium and a left atrium of a heart failure patient to communicate with each other; confirming hemodynamics of blood flow in a vicinity of the through-hole; and performing maintenance treatment for maintaining a size of the through-hole with a medical device comprising a shaft portion, an expandable and contractible expansion body disposed distal of the shaft portion, the expansion body including a plurality of linear expansion portions disposed at different positions in a circumferential direction of the shaft portion, each of the plurality of linear expansion portions including a concave portion recessed in a direction intersecting with an axial direction of the shaft portion, and a maintenance treatment element disposed in each of the linear expansion portions.

In accordance with an aspect, a treatment method is disclosed, the method comprising: expanding a through-hole formed in an atrial septum in a first expansion process to allow a right atrium and a left atrium of a heart failure patient to communicate with each other; expanding the through-hole more than in the first expansion process in a second expansion process; and performing maintenance treatment for maintaining the through-hole with respect to the through-hole after the second expansion process with a medical device comprising a shaft portion, an expandable and contractible expansion body disposed distal of the shaft portion, the expansion body including a plurality of linear expansion portions disposed at different positions in a circumferential direction of the shaft portion, each of the plurality of linear expansion portions including a concave portion recessed in a direction intersecting with an axial direction of the shaft portion, and a maintenance treatment element disposed in each of the linear expansion portions.

DETAILED DESCRIPTION

Set forth below with reference to the accompanying drawings is a detailed description of embodiments of a representing examples of the inventive medical device provided with a maintenance treatment element imparting energy to biological tissue and a treatment method performed on a heart failure patient. The dimensions or scales on the drawings may be exaggerated or different from actuality/reality for convenience of description and illustration. Hereinafter, an embodiment of the disclosure will be described with reference to the accompanying drawings. Note that the following description does not limit the technical scope and the meaning of terms used in the claims.

Figure 1:
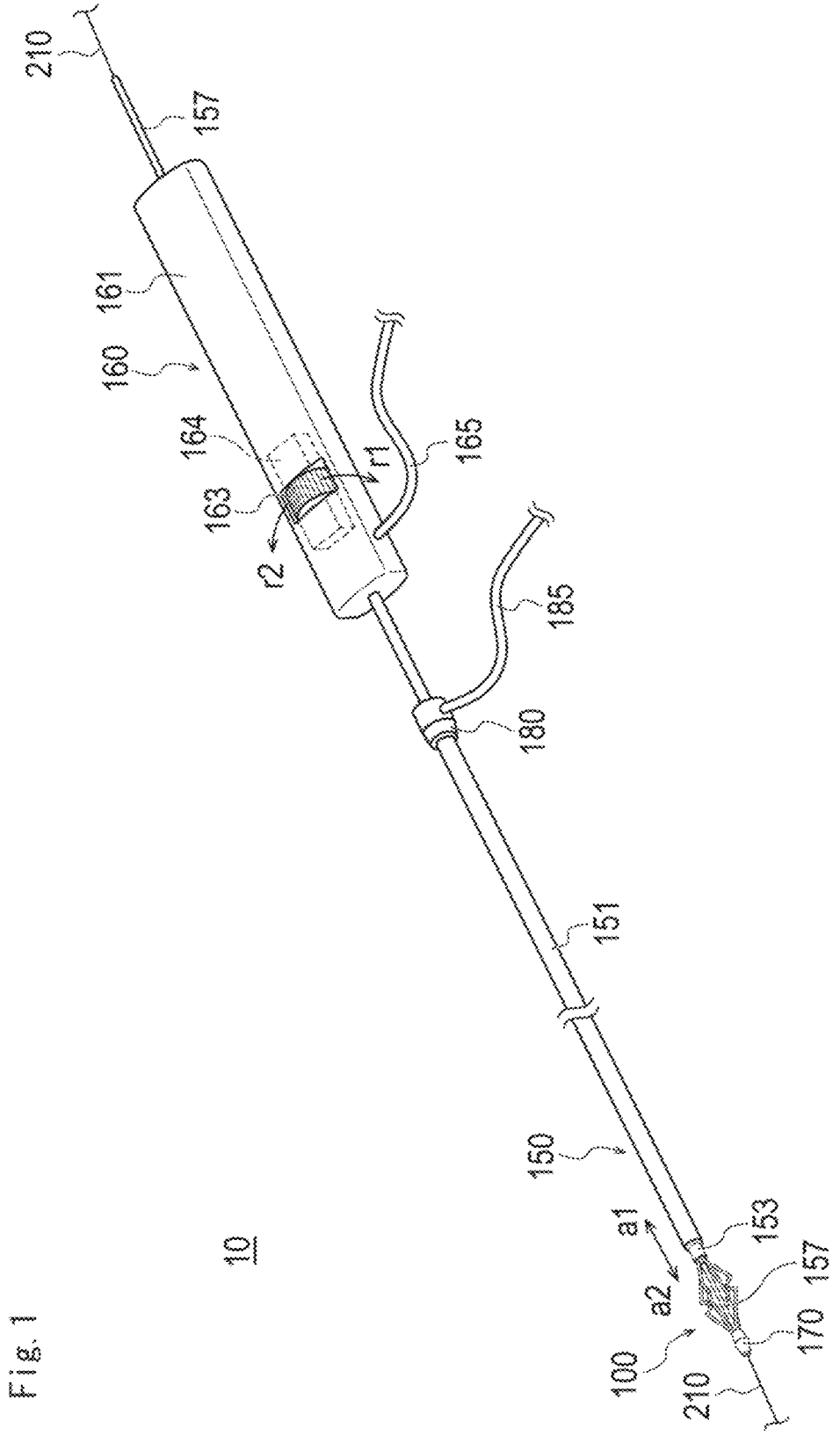
FIG. 1 is a perspective view schematically illustrating a medical device according to an embodiment of the disclosure.
Figure 13:
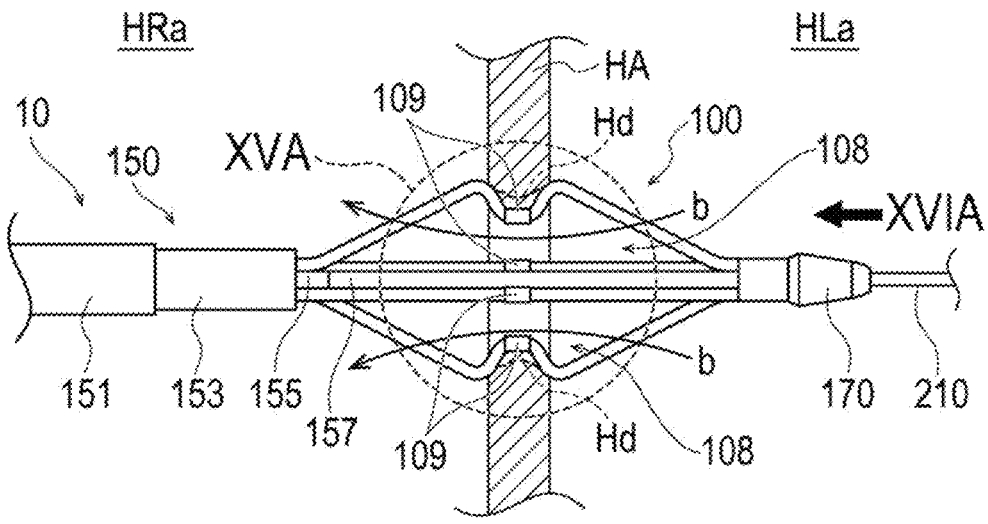
FIG. 13 is a diagram illustrating the treatment method according to the embodiment and is a cross-sectional view schematically illustrating a process of performing maintenance treatment on the through-hole formed in the atrial septum.
Figure 14:
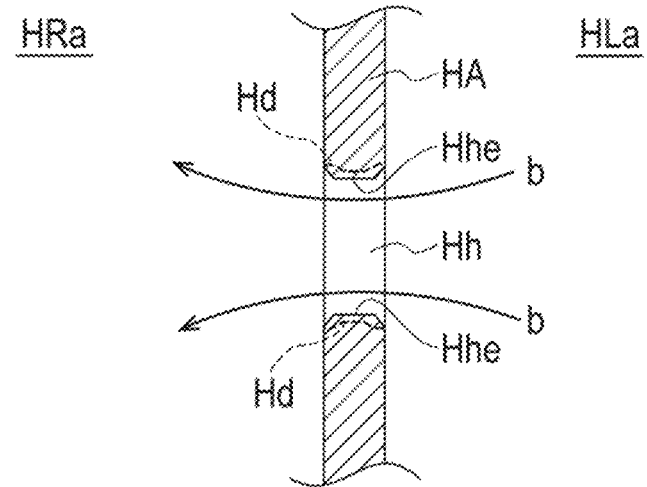
FIG. 14 is a diagram illustrating the treatment method according to the embodiment and is a cross-sectional view schematically illustrating a state after the expansion body of the medical device is removed from the through-hole formed in the atrial septum.

As illustrated in FIGS. 1, 13, and 14, a medical device 10 according to the present embodiment can be a device that can be used in a treatment method for alleviating or treating a heart failure symptom by expanding a through-hole Hh formed in an atrial septum HA of a patient's heart H to a predetermined size and maintaining the through-hole Hh at the predetermined size.

Figure 2:
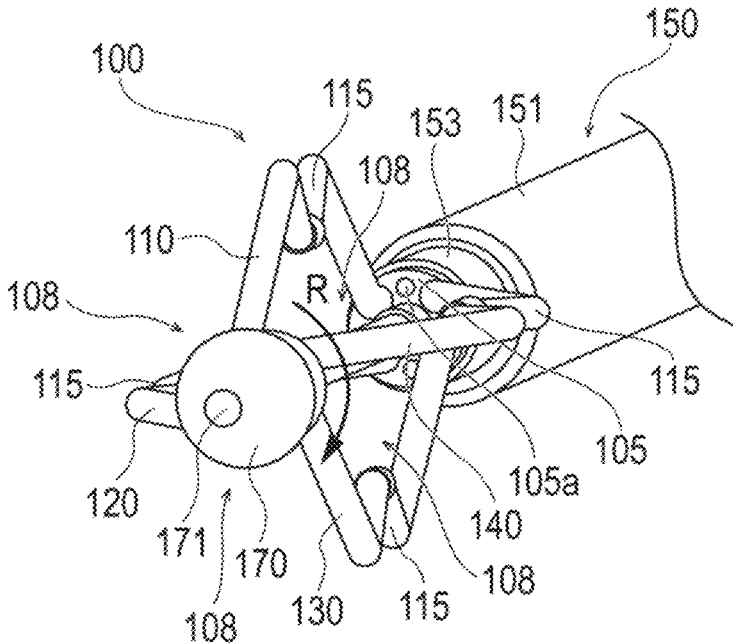
FIG. 2 is a perspective view in which the distal portion of the medical device according to the embodiment is viewed from the front side.
Figure 3:
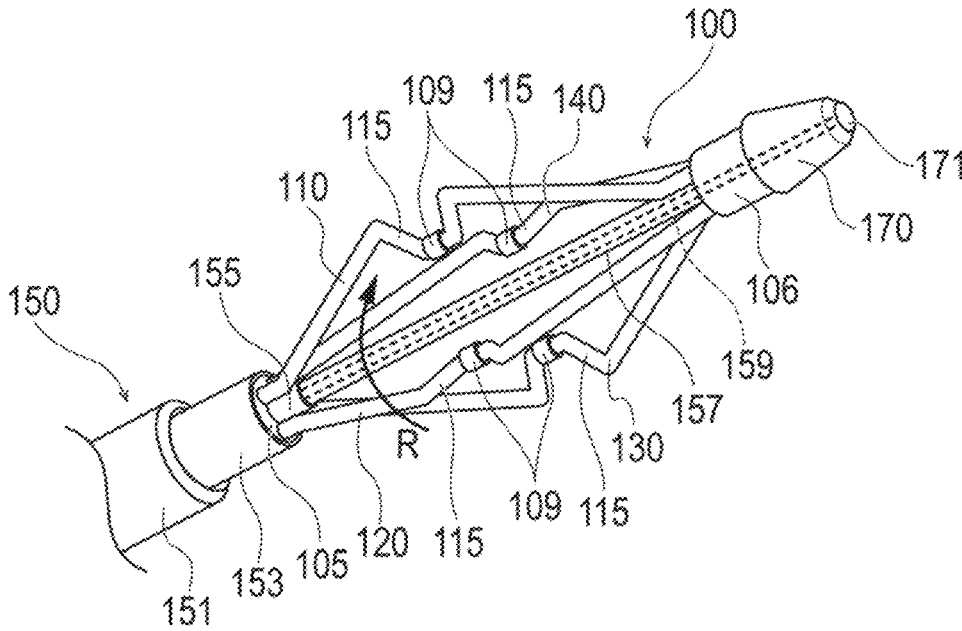
FIG. 3 is a perspective view in which the distal portion of the medical device according to the embodiment is viewed from the lower side.
Figure 4:
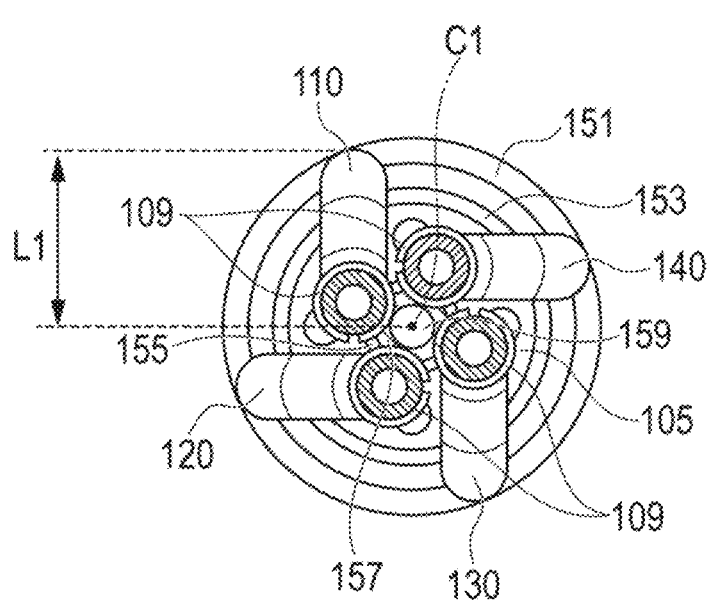
FIG. 4 is a cross-sectional view of a maintenance treatment element portion at a time when the distal portion of the medical device according to the embodiment is viewed from the front and is a diagram illustrating a state where an expansion body is stored in a storage sheath.
Figure 5:
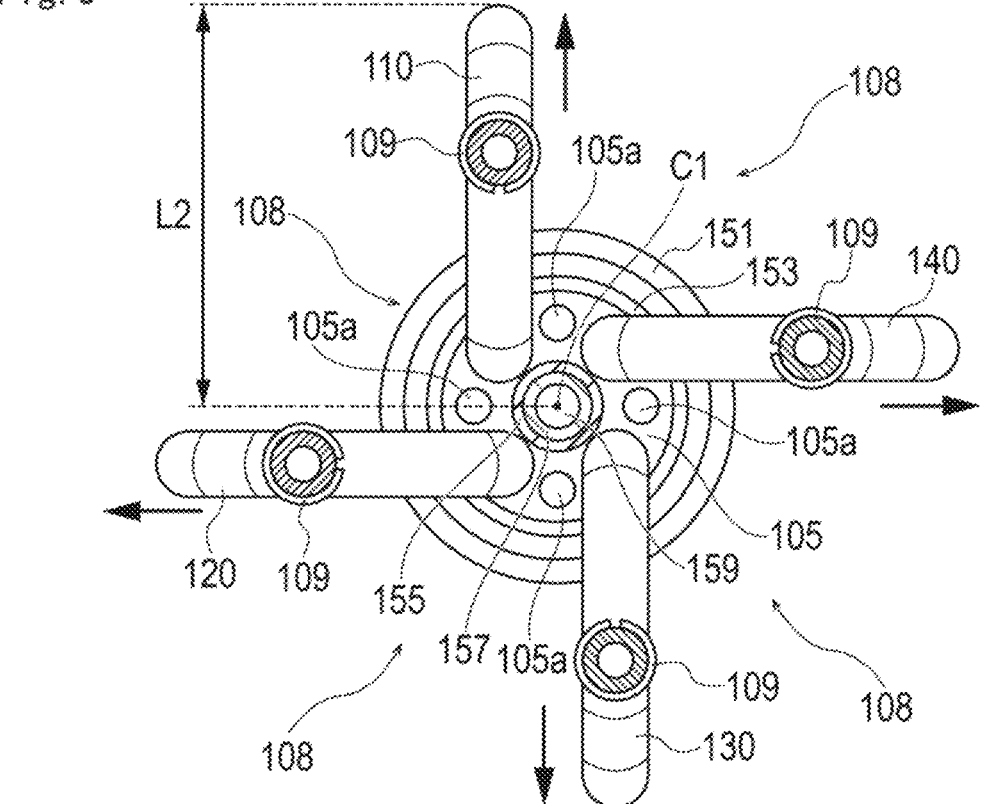
FIG. 5 is a cross-sectional view of the maintenance treatment element portion at a time when the distal portion of the medical device according to the embodiment is viewed from the front and is a diagram illustrating a state where the expansion body is exposed from the storage sheath.

FIGS. 1 to 5 are diagrams illustrating each portion of the medical device 10. FIG. 1 is a perspective view illustrating an overall configuration of the medical device 10, FIGS. 2 and 3 are perspective views illustrating the distal portion side of the medical device 10 in an enlarged manner, and FIGS. 4 and 5 are front views illustrating the storage form of an expansion body 100.

Figure 6:
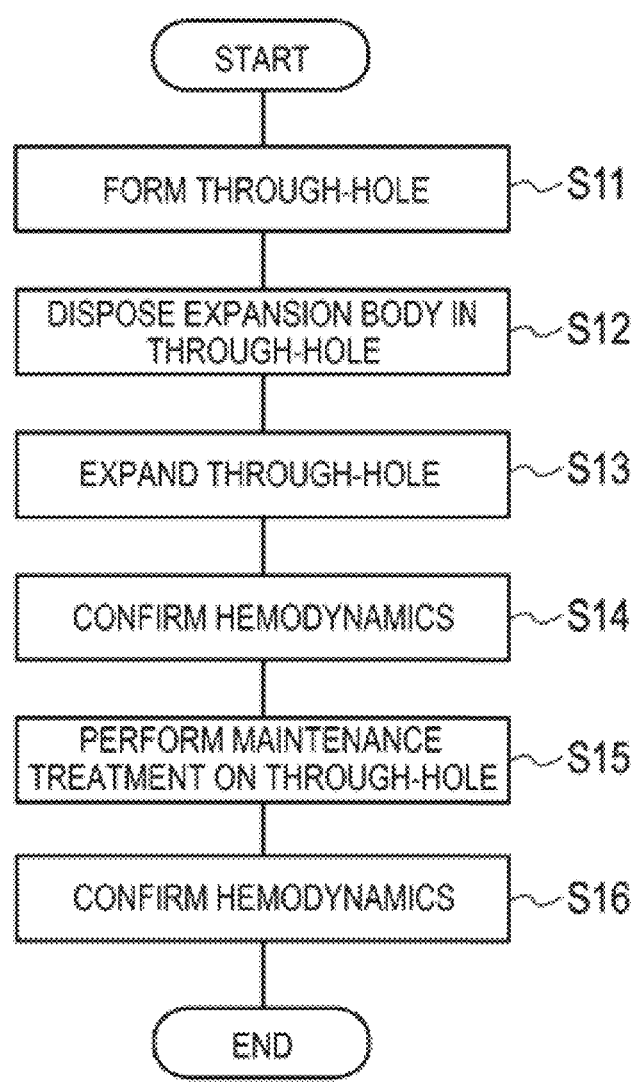
FIG. 6 is a flowchart illustrating the procedure of a treatment method according to the embodiment.
Figure 7:
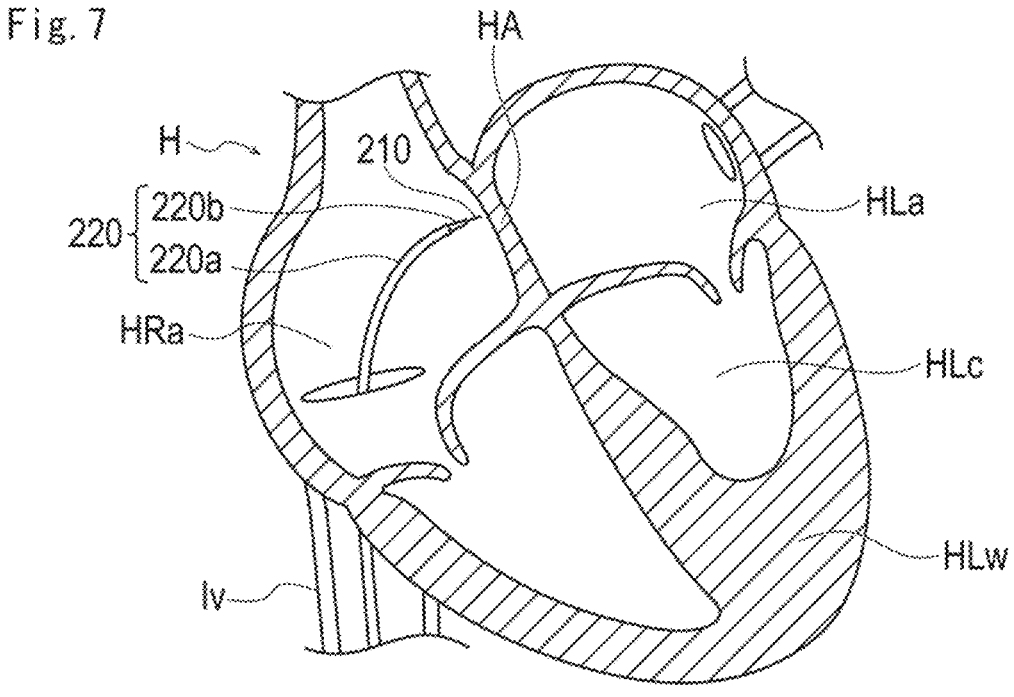
FIG. 7 is a diagram illustrating the procedure of the treatment method according to the embodiment and is a cross-sectional view schematically illustrating a patient's heart.
Figure 8:
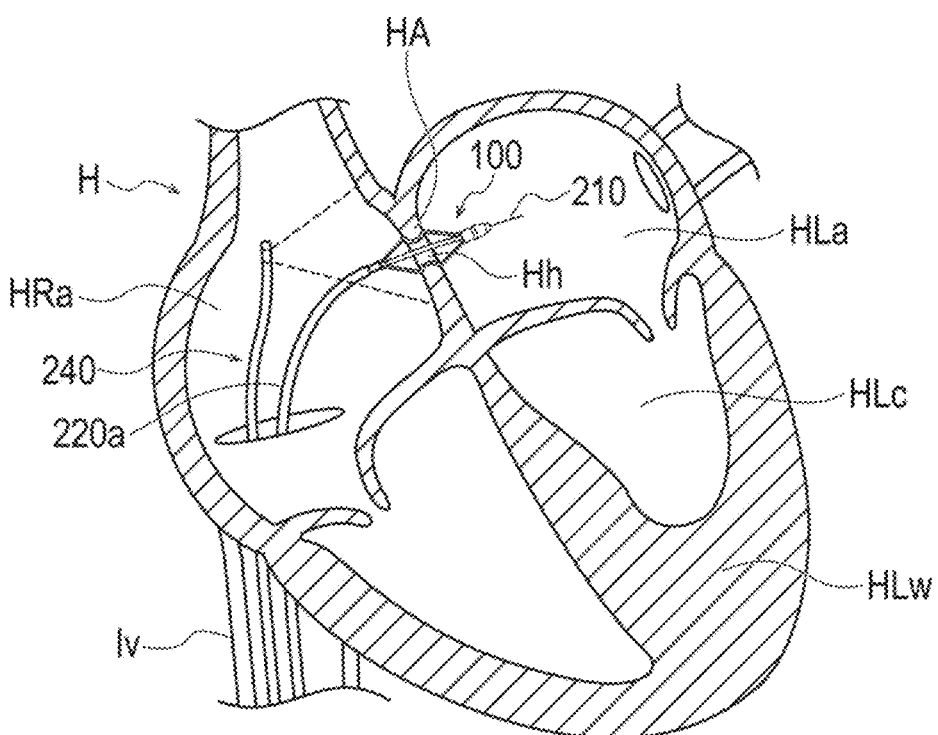
FIG. 8 is a diagram illustrating the procedure of the treatment method according to the embodiment and is a cross-sectional view schematically illustrating a process of confirming the hemodynamics in the vicinity of a through-hole formed in the atrial septum.

In addition, FIGS. 6 to 16 are diagrams illustrating a treatment method using the medical device 10. FIG. 6 is a diagram illustrating a flowchart schematically illustrating each process of the treatment method, FIGS. 7 and 8 are diagrams schematically illustrating some of the processes of the treatment method together with the patient's heart H, and FIGS. 9 to 16 are cross-sectional views illustrating each process of the treatment method.

In the description of the specification, the side of the medical device 10 that is inserted into a living body (side where the expansion body 100 is disposed) is referred to as the distal side or distal end, a hand operation unit 160 side of the medical device 10 is referred to as the proximal side or proximal end, and the direction in which a shaft portion 150 extends is referred to as the axial direction. In addition, the distal portion in the description of the specification means a predetermined range from the distal end (the most distal end) to the proximal side and the proximal portion in the description of the specification means a predetermined range from the proximal end (the most proximal end) to the distal side.

Hereinafter, the medical device 10 and the treatment method will be described in detail.

As illustrated in FIGS. 1 to 3, the medical device 10 can include the elongated shaft portion 150, the expandable and contractible expansion body 100 provided on the distal side of the shaft portion 150, and a maintenance treatment element (energy transmission element) 109 disposed in the expansion body 100 and imparting energy to biological tissue.

The expansion body 100 will be described.

As illustrated in FIGS. 2 and 3, the expansion body 100 includes a plurality of expansion portions 110, 120, 130, and 140 disposed at different positions in the circumferential direction of the shaft portion 150 (R direction in the drawings).

In accordance with an exemplary embodiment, each of the expansion portions 110, 120, 130, and 140 is configured to be expandable and contractible. In the present embodiment, a state where the expansion body 100 is expanded means that each of the expansion portions 110, 120, 130, and 140 is in an expanded state and a state where the expansion body 100 is contracted means that each of the expansion portions 110, 120, 130, and 140 is in a contracted state. Note that a state at a time when the expansion body 100 is expanded is illustrated in FIGS. 1 to 3.

In addition, in the following description of the specification, the expansion portion 110 is referred to as the first expansion portion and, similarly, the expansion portion 120, the expansion portion 130, and the expansion portion 140 are respectively referred to as the second expansion portion, the third expansion portion, and the fourth expansion portion for convenience. Note that the expansion portions 110, 120, 130, and 140 have substantially the same configuration (i.e., shape) and thus a specific configuration will be described with the first expansion portion 110 used as an example and description of the other expansion portions 120, 130, and 140 omitted as appropriate.

In accordance with an exemplary embodiment, the first expansion portion 110 includes a predetermined concave portion 115 in an expanded and deformed state. The concave portion 115 has a shape recessed in a concave shape in a direction intersecting with the axial direction of the shaft portion 150 (in the up-down direction illustrated in FIG. 2). In accordance with an exemplary embodiment, the maintenance treatment element 109, which imparts energy to an edge portion Hhe of the through-hole Hh formed in the atrial septum HA, is disposed in the concave portion 115 (see FIG. 15).

The concave portion 115, which is formed in the expansion body 100 (each of the expansion portions 110, 120, 130, and 140), may be formed at least in a state where the expansion body 100 is expanded. For example, the concave portion 115 may be present in both a state where the expansion body 100 is not expanded and a state where the expansion body 100 is expanded. In addition, the size of the concave portion 115 (amount by which the concave portion 115 is recessed with respect to the axial direction) with respect to the degree of expansion (expansion amount) of the expansion body 100 is not particularly limited insofar as the concave portion 115 can be disposed with respect to a treatment target site (such as the edge portion Hhe of the through-hole Hh formed in the atrial septum HA) during treatment by means of the maintenance treatment element 109. In addition, the expansion portions provided in the expansion body 100 can be appropriately changed, for example, in terms of number, shape, and so on.

The concave portion 115 is formed in each of the plurality of expansion portions 110, 120, 130, and 140 included in the expansion body 100. The maintenance treatment element 109 is disposed in the concave portion 115 formed in each of the expansion portions 110, 120, 130, and 140. Accordingly, in performing treatment with the medical device 10, a surgeon such as a doctor can simultaneously perform the treatment at four locations via the maintenance treatment element 109 disposed in each of the expansion portions 110, 120, 130, and 140 (see FIG. 16).

As illustrated in FIGS. 2 and 3, a linear member shaped in advance to form the concave portion 115 when expanded to deform constitutes each of the expansion portions 110, 120, 130, and 140 included in the expansion body 100.

The expansion body 100 is configured such that the four expansion portions 110, 120, 130, and 140 disposed on the distal side expand and contract as a pulling shaft 157 (see FIG. 1, described later) is pushed and pulled (i.e., moved in a distal direction and a proximal direction).

As illustrated in FIG. 3, a base portion 105 to which each of the expansion portions 110, 120, 130, and 140 is integrally connected is formed on the respective proximal sides of the expansion portions 110, 120, 130, and 140. In addition, a distal portion 106 to which each of the expansion portions 110, 120, 130, and 140 is integrally connected is formed on the respective distal sides of the expansion portions 110, 120, 130, and 140.

The linear member that constitutes each of the expansion portions 110, 120, 130, and 140 can be made of, for example, a metal material having a circular cross-sectional shape and a relatively small diameter. In a case where the linear member is made of the metal material, for example, an alloy having spring properties such as a titanium-based (Ti—Ni, Ti—Pd, Ti—Nb—Sn, or the like) alloy, a copper-based alloy, stainless steel (SUS304), β titanium steel, a Co—Cr alloy, and a nickel-titanium alloy can be used. However, the linear member is not particularly limited in terms of material, cross-sectional shape, and outer diameter, and any material, cross-sectional shape, and outer diameter can be selected.

In addition, as will be described later, positioning during the treatment by means of the maintenance treatment element 109 is performed on each of the expansion portions 110, 120, 130, and 140 by the concave portion 115 being fitted (engaged) with respect to the edge portion Hhe of the through-hole Hh formed in the atrial septum HA (see FIG. 15). At this time, it is preferable that each of the expansion portions 110, 120, 130, and 140 has a certain degree of hardness such that each of the expansion portions 110, 120, 130, and 140 is not displaced from the edge portion Hhe of the through-hole Hh. From this perspective, it is preferable that each of the expansion portions 110, 120, 130, and 140 has a wire diameter, for example, of 0.3 mm to 0.8 mm and is formed of a material such as a Ni—Ti alloy in a case where, for example, a wire having a circular cross section is used.

In addition, as for the expansion portions 110, 120, 130, and 140, a dimension L1 of the maximum outer shape during contraction (dimension in the up-down or left-right direction from a central axis C1 of the shaft portion 150 illustrated in FIG. 4) can be, for example, 1 mm to 3 mm and a dimension L2 of the maximum outer shape during expansion (dimension in the up-down or left-right direction from the central axis C1 of the shaft portion 150 illustrated in FIG. 5) can be, for example, 4 mm to 15 mm.

Figure 15:
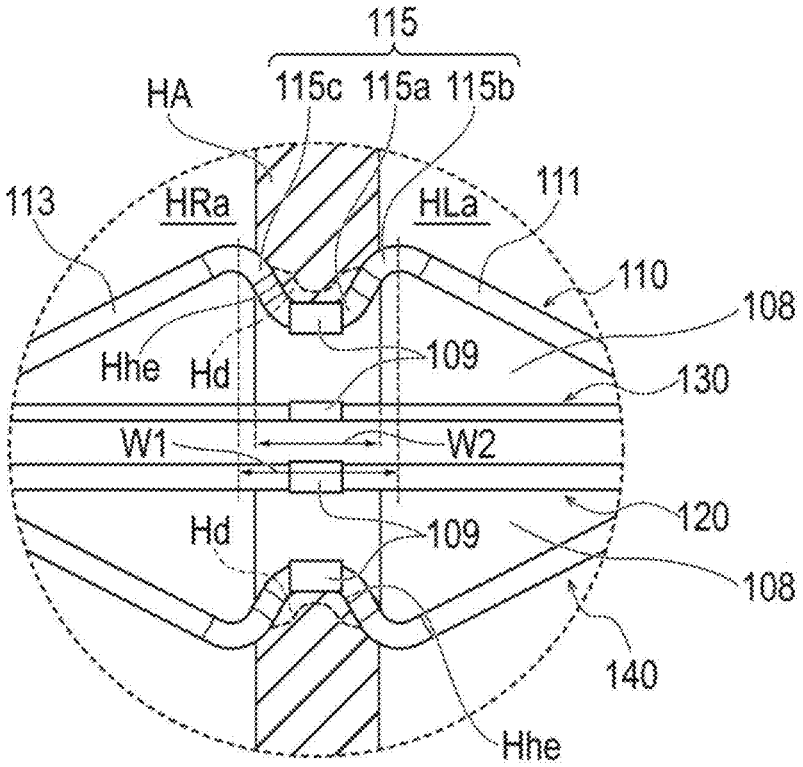
FIG. 15 is an enlarged view illustrating the broken line portion XVA part illustrated in FIG. 13.

An enlarged view of the expansion body 100 that is expanded is illustrated in FIG. 15.

As illustrated in FIG. 15, the first expansion portion 110 includes a distal side inclined portion 111 inclined obliquely toward the axial center side of the shaft portion 150, a proximal side inclined portion 113 inclined obliquely toward the axial center side of the shaft portion 150, and the concave portion 115 extending between the distal side inclined portion 111 and the proximal side inclined portion 113.

The concave portion 115 includes a bottom portion (i.e., most recessed portion) 115a extending along the axial direction (left-right direction in FIG. 15), a distal side standing portion 115b formed on the distal side in the axial direction as compared with the bottom portion 115a (to the right of the bottom portion 115a in FIG. 15) and rising in a direction intersecting with the axial direction (upward in FIG. 15) from the bottom portion 115a, and a proximal side standing portion 115c formed on the proximal side in the axial direction as compared with the bottom portion 115a (to the left of the bottom portion 115a in FIG. 15) and rising in a direction intersecting with the axial direction (upward in FIG. 15) from the bottom portion 115a. Note that the distal side standing portion 115b and the proximal side standing portion 115c are formed so as to have substantially the same length dimension in the direction of expansion (height direction intersecting with the axial direction) in the expanded state.

The maintenance treatment element 109 is disposed in the bottom portion 115a of the concave portion 115. Accordingly, when the concave portion 115 is disposed with respect to the edge portion Hhe of the through-hole Hh formed in the atrial septum HA as illustrated in FIG. 15, the maintenance treatment element 109 disposed in the bottom portion 115a of the concave portion 115 comes into contact with the edge portion Hhe of the through-hole Hh. In addition, the first expansion portion 110 holds the relative positions of the maintenance treatment element 109 and the edge portion Hhe of the through-hole Hh and help prevent displacement between the maintenance treatment element 109 and the edge portion Hhe of the through-hole Hh by containing a part of the edge portion Hhe of the through-hole Hh in the concave portion 115.

As illustrated in FIG. 15, a dimension (width dimension) W1 of the concave portion 115 of the first expansion portion 110 along the axial direction can be formed larger than, for example, a dimension W2 of the edge portion Hhe of the through-hole Hh along the axial direction. Note that the width dimension W1 of the concave portion 115 is the length of a straight line segment interconnecting the part where the distal side standing portion 115b rises most and the part where the proximal side standing portion 115c rises most in the present embodiment. In a case where the concave portion 115 has the width dimension described above, the edge portion Hhe of the through-hole Hh can be more reliably contained in the concave portion 115, and thus it is possible to suitably prevent the edge portion Hhe of the through-hole Hh from being displaced from the concave portion 115. The width dimension W1 of the concave portion 115 can be, for example, 1 mm to 8 mm.

The maintenance treatment element 109 can be formed in, for example, the entire concave portion 115 (entire region including the bottom portion 115a, the distal side standing portion 115b, and the proximal side standing portion 115c). In addition, the maintenance treatment element 109 can be disposed in, for example, the entire region of the bottom portion 115a that is in contact with the edge portion Hhe of the through-hole Hh (entire region of the bottom portion 115a in the axial direction). By the maintenance treatment element 109 being disposed as in each of the disposition examples described above, the maintenance treatment element 109 can be more reliably brought into contact with the edge portion Hhe of the through-hole Hh, and thus heat can be suitably imparted to the edge portion Hhe of the through-hole Hh. In addition, the concave portion 115 may be formed at least in the expanded state of the expansion body 100 and the concave portion 115 may not be formed in the expansion body 100 that is yet to be expanded (that is in the contracted state).

In addition, in a case where the plurality of expansion portions 110, 120, 130, and 140 constitute the expansion body 100 as in the present embodiment, the expansion portions 110, 120, 130, and 140 may have different positions where the maintenance treatment element 109 is disposed and the maintenance treatment element 109 may be disposed at the same position or a different position for each expansion portion. Further, the maintenance treatment element 109 can be disposed at, for example, any position for each expansion portion also in a case where the maintenance treatment element 109 is disposed at a position other than the bottom portion 115*a* of the concave portion 115 as will be described later (see FIG. 23).

As illustrated in FIGS. 13 and 14, the expansion body 100 includes a circulation portion 108 allowing blood flow (indicated by an arrow b in each of the drawings) via the through-hole Hh in a state where the concave portion 115 is disposed in the through-hole Hh formed in the atrial septum HA of the patient.

As illustrated in FIGS. 2 and 5, when each of the expansion portions 110, 120, 130, and 140 is expanded, that is, when the expansion body 100 is expanded, the expansion portions 110, 120, 130, and 140 form gaps (spaces) along the circumferential direction. As illustrated in FIGS. 13 and 14, the expansion body 100 that is inserted in the through-hole Hh allows blood to flow from a left atrium HLa of the heart to a right atrium HRa of the heart via the circulation portion 108 that the gaps constitute.

In a case where the expansion body 100 is provided with four expansion portions as in the present embodiment, four circulation portions (gaps) 108 having substantially the same size are formed between the expansion portions. Note that the circulation portion 108 is not particularly limited in terms of shape, size, structure, number, and so on. For example, a hole formed in the expansion body, a notch formed in the expansion body, or the like is capable of constituting the circulation portion 108 as will be described later (see, for example, FIGS. 31 and 34).

The expansion body 100 (such as each of the expansion portions 110, 120, 130, and 140) can be provided with an X-ray contrast marker. The X-ray contrast marker can be formed at, for example, a location indicating the position of the maintenance treatment element 109 in the expansion body 100. The X-ray contrast marker can be, for example, a radiopaque material, examples of which include metals such as platinum, gold, silver, titanium, and tungsten and alloys of the metals.

The maintenance treatment element 109 disposed in the expansion body 100 is capable of including, for example, a heating element (electrode chip) generating heat by receiving high-frequency electric energy from an external energy supply device (not illustrated). The maintenance treatment element 109 and the energy supply device are interconnected by a conductive wire (lead wire) coated with an insulating coating material (not illustrated). The conductive wire is electrically connected to the maintenance treatment element 109 disposed in each of the expansion portions 110, 120, 130, and 140 with a lumen 105*a* (described later) inserted. The lumen 105*a* is formed in the base portion 105 of the expansion body 100.

A known high-frequency power source device incorporating, for example, a central processing unit (CPU) having a function as a control unit is capable of constituting the energy supply device. The supply of high-frequency to the maintenance treatment element 109, and the stopping of the energy supply, and the like can be controlled via, for example, a CPU or the like.

In accordance with an exemplary embodiment, the maintenance treatment element 109 can be configured as a monopolar electrode. In this case, a counter electrode plate (not illustrated) or the like is used when treatment is performed by means of the medical device 10. During the treatment by means of the medical device 10, an electric current can be applied to the edge portion Hhe of the through-hole Hh formed in the atrial septum HA by the counter electrode plate being attached to a patient's body surface and a pseudo current circuit being formed between the maintenance treatment element 109, the patient, and the counter electrode plate.

The maintenance treatment element 109 may include, for example, a bipolar electrode that allows an electric current to flow between the expansion portions 110, 120, 130, and 140. In addition, although the maintenance treatment element 109 of the medical device 10 is configured to be capable of performing ablation by means of high-frequency electric energy, an energy transmission element capable of imparting energy to the edge portion Hhe of the through-hole Hh, and wherein examples of the energy transmission element can include one that performs heating or cooling by means of microwave energy, ultrasound energy, coherent light such as laser, a heated fluid, a cooled fluid, or a chemical medium, one that generates frictional heat, and a heater provided with an electric wire, is capable of constituting the maintenance treatment element 109 and specific forms of the maintenance treatment element 109 are not particularly limited.

Next, the shaft portion 150 will be described.

As illustrated in FIGS. 1, 2, and 3, the shaft portion 150 includes a storage sheath 151 capable of storing the expansion body 100 that is contracted, an outer shaft 153 inserted through the storage sheath 151, an inner shaft 155 inserted through the outer shaft 153, the pulling shaft 157 inserted through the inner shaft 155, and a distal tip 170 disposed at the distal end of the shaft portion 150.

In accordance with an exemplary embodiment, the storage sheath 151 stores the expansion body 100 that is contracted (i.e., in a contracted state). The storage sheath 151 is configured to be capable of moving forward and backward along the axial direction of the shaft portion 150. When the expansion body 100 is expanded, the storage sheath 151 is moved to the proximal side with respect to the expansion body 100, and then the expansion body 100 is exposed (protrudes) from the distal end of the storage sheath 151.

In accordance with an exemplary embodiment, a surgeon such as a doctor grasps the storage sheath 151 with his or her fingers and moves the storage sheath 151 forward and backward, and then the storage sheath 151 can be moved along the axial direction of the shaft portion 150. In addition, a liquid supply section (such as a three-way stopcock) 180 for supplying a priming liquid between the storage sheath 151 and the outer shaft 153, and a tube 185 connected to the liquid supply section 180 can be provided as illustrated in FIG. 1.

The outer shaft 153 is configured such that the distal side of the outer shaft 153 is capable of protruding from the storage sheath 151 and the proximal side of the outer shaft 153 is connected to a hand operation unit 160. As illustrated in FIG. 3, the base portion 105 of the expansion body 100 is inserted through the lumen of the outer shaft 153.

A tubular member stretching in the axial direction constitutes the base portion 105 of the expansion body 100. As illustrated in FIG. 5, the inner shaft 155 is inserted through the base portion 105 of the expansion body 100. In addition, the pulling shaft 157 is inserted through the lumen of the inner shaft 155.

As illustrated in FIG. 3, the inner shaft 155 protrudes to the distal side of the outer shaft 153. The pulling shaft 157 has a proximal side extending to the proximal side of the hand operation unit 160 (see FIG. 1) and a distal side extending to the distal side of the inner shaft 155. In addition, the distal end of the pulling shaft 157 is connected to the distal portion 106 of the expansion body 100. The pulling shaft 157 is configured such that the pulling shaft 157 can be moved forward and backward along the axial direction by an operation dial 163 (described later).

As illustrated in FIGS. 1 to 3, the expansion body 100 is configured to be expandable and deformable in a state of being exposed from the storage sheath 151 and disposed between the storage sheath 151 and the distal tip 170. A surgeon can move the distal portion 106 of the expansion body 100 connected to the pulling shaft 157 to the proximal side by moving the pulling shaft 157 to the proximal side. This operation results in a decrease in the distance between the distal portion 106 of the expansion body 100 and the base portion 105 of the expansion body 100. As illustrated in FIGS. 2 and 3, the expansion body 100 expands in a direction intersecting with the axial direction (in the up-down or left-right direction in FIG. 2) while contracting in the axial direction.

As illustrated in FIG. 3, a guide wire lumen 159 extending in the axial direction is formed in the pulling shaft 157, the distal portion 106 of the expansion body 100 disposed on the distal side of the pulling shaft 157, and the distal tip 170 disposed on the distal side of the distal portion 106 of the expansion body 100. As illustrated in FIG. 1, during treatment by means of the medical device 10, movements of the shaft portion 150 and the expansion body 100 can be guided by a guide wire 210 by the guide wire 210 being inserted through the guide wire lumen 159.

As illustrated in FIGS. 2 and 5, the lumen 105*a* is formed in the base portion 105 of the expansion body 100. The conductive wire (not illustrated) connected to the maintenance treatment element 109 is inserted through the lumen 105*a*. The conductive wire can be disposed along, for example, the inside of each of the expansion portions 110, 120, 130, and 140. As a result of the disposition described above, the conductive wire can be prevented from hindering a smooth treatment by being disposed on the concave portion 115 during treatment by means of the expansion body 100. Note that the conductive wire is, for example, extends (i.e., led out) from the proximal side of the hand operation unit 160 and electrically connected to an energy supply source (not illustrated) as an external device via, for example, a predetermined connector similar to the pulling shaft 157.

As illustrated in FIG. 3, the distal tip 170 has a tapered shape having an outer shape becoming smaller toward the distal side. An opening portion 171 for leading the guide wire 210 out to the distal side is formed at the distal end of the distal tip 170. In accordance with an exemplary embodiment, the distal tip 170 has a function of preventing, for example, a biological tissue injury when the medical device 10 is moved into a living body and a function of assisting insertion of the medical device 10 through the through-hole Hh formed in the atrial septum HA during the insertion. In accordance with an exemplary embodiment, the distal tip 170 can have X-ray contrast properties.

In a case where the expansion body 100 is provided with the four expansion portions 110, 120, 130, and 140 as in the present embodiment, each of the expansion portions 110, 120, 130, and 140 can be stored in, for example, the storage sheath 151 as illustrated in FIG. 4.

Specifically, each of the expansion portions 110, 120, 130, and 140 can be disposed so as not to overlap the central axis C1 of the shaft portion 150 in the up-down direction and the left-right direction when viewed from the front. In other words, the expansion portions 110, 120, 130, and 140 are not disposed at circumferentially facing positions with respect to the central axis C1. For example, the first expansion portion 110 and the third expansion portion 130 facing each other in the up-down direction can be disposed so as to be displaced in the left-right direction in FIGS. 4 and 5 with respect to the central axis C1 of the shaft portion 150. In addition, the second expansion portion 120 and the fourth expansion portion 140 facing each other in the left-right direction can be disposed so as to be displaced in the up-down direction in FIGS. 4 and 5 with respect to the central axis C1 of the shaft portion 150. As illustrated in FIG. 4, when the expansion portions 110, 120, 130, and 140 are disposed in this manner and the expansion body 100 is stored in the storage sheath 151, the respective contraction directions of the expansion portions 110, 120, 130, and 140 do not overlap each other in the up-down and left-right directions when viewed from the front, and thus the shape of the expansion body 100 during contraction becomes relatively small. As a result, the expansion body 100 can be stored in the storage sheath 151 relatively more compactly and the diameter of the storage sheath 151 can be reduced.

The storage sheath 151, the outer shaft 153, and the inner shaft 155 can be made of, for example, a resin material generally used for a catheter or the like. Examples of the resin material of the storage sheath 151, the outer shaft 153, and the inner shaft 155 can include polyethylene, polypropylene, an ethylene-propylene copolymer, a polyolefin such as an ethylene-vinyl acetate copolymer, a thermoplastic resin such as soft polyvinyl chloride, various types of rubber such as silicone rubber and latex rubber, various elastomers such as a polyurethane elastomer, a polyamide elastomer, and a polyester elastomer, and crystalline plastics such as polyimide, crystalline polyethylene, and crystalline polypropylene can be used. In addition, a mesh structure or the like woven from stainless steel or the like can be added as a reinforcement body to the resin material.

The pulling shaft 157 can be made of what is configured by an elongated wire. The elongated wire can be made from, for example a super elastic alloy such as a nickel-titanium alloy and a copper-zinc alloy, a metal material such as stainless steel, and a resin material having a relatively high rigidity, being coated with a resin material such as polyvinyl chloride, polyethylene, polypropylene, and an ethylene-propylene copolymer.

The distal tip 170 can be formed of, for example, a polymer material such as a polyolefin, polyvinyl chloride, a polyamide, a polyamide elastomer, polyurethane, a polyurethane elastomer, polyimide, and fluororesin or a mixture of the polymer materials or a multilayer tube of the two or more polymer materials.

Next, the hand operation unit 160 will be described.

As illustrated in FIG. 1, the hand operation unit 160 includes a housing 161, the operation dial 163 disposed in the housing 161, and a conversion mechanism 164 converting the rotational operation of the operation dial 163 into a forward and backward movement of the pulling shaft 157.

In accordance with an exemplary embodiment, the housing 161 can be a case that can be grasped, for example, with the fingers of the operator or surgeon. The conversion mechanism 164 illustrated in a simplified manner is disposed in the housing 161. The operation dial 163 is disposed with a part of the operation dial 163 exposed from the housing 161 and can be rotated in the r1-r2 direction in FIG. 1 by being operated via fingers. The pulling shaft 157, which operates the expansion and contraction of the expansion body 100, is connected to the operation dial 163 via the conversion mechanism 164.

When the operation dial 163 is rotated in the arrow r1 direction, the medical device 10 moves the pulling shaft 157 to the proximal side and expands the expansion body 100 in conjunction with the movement. In addition, when the operation dial 163 is rotated in the arrow r2 direction, the medical device 10 moves the pulling shaft 157 to the distal side and contracts the expansion body 100 in conjunction with the movement. The conversion mechanism 164 is capable of including, for example, a rack and pinion mechanism converting the rotation of the operation dial 163 into a forward and backward movement (linear movement) of the pulling shaft 157.

Note that the combination between the direction of rotation of the operation dial 163 and the direction of movement of the pulling shaft 157 can be changed as appropriate. In addition, the hand operation unit 160 can be provided with a mechanism moving the pulling shaft 157 forward and backward not in conjunction with the rotary operation of the operation dial 163.

As illustrated in FIG. 1, the hand operation unit 160 can be provided with a tube 165 for supplying a priming liquid (i.e., priming solution) between the inner shaft 155 and the pulling shaft 157. In accordance with an exemplary embodiment, a valve body that helps prevents the priming liquid supplied via the tube 165 from flowing into the proximal side of the housing 161 can be appropriately disposed in the housing 161.

The housing 161 of the hand operation unit 160 cam be made of a relatively hard resin material, a metal material, or the like.

Next, the treatment method according to the present embodiment will be described.

The treatment method according to the present embodiment includes various treatments performed on a patient suffering from heart failure (left heart failure). More specifically, the treatment method is treatment performed on a patient suffering from chronic heart failure in which the blood pressure of the left atrium HLa of heart H increases as the myocardium of a left ventricle HLw of the heart H is enlarged to result in an increase in stiffness (hardness) as illustrated in FIG. 7.

Referring to FIG. 6, the treatment method includes in summary a process of forming the through-hole Hh in the atrial septum HA of the heart H (S11), a process of disposing the expansion body 100 in the through-hole Hh (S12), a process of expanding the through-hole Hh (S13), a process of confirming the hemodynamics in the vicinity of the through-hole Hh (S14), a process of performing maintenance treatment for maintaining the size of the through-hole Hh (S15), and a process of confirming the hemodynamics in the vicinity of the through-hole Hh after the maintenance treatment (S16). Hereinafter, each process will be described.

In forming the through-hole Hh, a surgeon such as a doctor delivers an introducer 220, in which a guiding sheath 220a and a dilator 220b are combined, to the vicinity of the atrial septum HA of the heart H as illustrated in FIG. 7. The introducer 220 can be delivered to the right atrium HRa of the heart H via, for example, an inferior vena cava Iv. In addition, the introducer 220 can be delivered by means of the guide wire 210 known in the medical field. The surgeon can deliver the introducer 220 along the guide wire 210 by inserting the guide wire 210 through the dilator 220b.

Note that the insertion of the introducer 220 into a living body and the insertion of the guide wire 210 can be performed by a method known in the medical field (method using, for example, an introducer for blood vessel introduction).

Next, the surgeon performs the process (S11) of forming the through-hole Hh in the atrial septum HA of the heart H.

Figure 9:
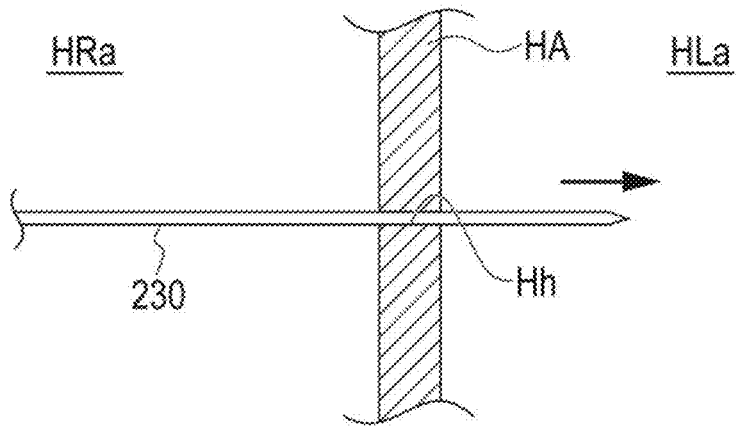
FIG. 9 is a diagram illustrating the treatment method according to the embodiment and is a cross-sectional view schematically illustrating a process of forming the through-hole in the atrial septum.

As illustrated in FIG. 9, the through-hole Hh is formed in the atrial septum HA by the surgeon by a predetermined puncture device 230 penetrating the atrial septum HA from the right atrium HRa side toward the left atrium HLa side. A device such as a wire having a sharp distal end can be used as the puncture device 230. The puncture device 230 is inserted through the dilator 220b illustrated in FIG. 7 and delivered to the atrial septum HA. The puncture device 230 can be delivered to the atrial septum HA instead of the guide wire 210 after the guide wire 210 is removed from the dilator 220b.

After the through-hole Hh is formed by the puncture device 230, the surgeon can widen the through-hole Hh by inserting the dilator 220b through the through-hole Hh. Next, the surgeon removes the puncture device 230 from the dilator 220b. After removing the puncture device 230, the surgeon delivers the guide wire 210 to the left atrium HLa through the introducer 220. Subsequently, the dilator 220b and the guiding sheath 220a are removed with the guide wire 210 left.

In accordance with an exemplary embodiment, the surgeon may perform the process (S11) of forming the through-hole Hh in the atrial septum HA by using the medical device 10 instead of the introducer 220. In this case, the storage sheath 151 of the medical device 10 can be used in place of the guiding sheath 220a and the distal tip 170 of the medical device 10 can be used in place of the dilator 220b. In a case where the medical device 10 is used instead of the introducer 220 as described above, it is possible to proceed to the next process without removing the medical device 10 after the through-hole Hh is widened by the distal tip 170. In addition, the distal end of the medical device 10 can be provided with, for example, a function of puncturing the atrial septum HA. As a result, the atrial septum HA can be punctured by the medical device 10 and the through-hole Hh can be widened.

Note that the specific structure of the puncture device 230 used for the penetration of the atrial septum HA, the specific procedure for forming the through-hole Hh is not limited to the content described above.

Next, the surgeon performs the process (S12) of disposing the expansion body 100 in the through-hole Hh.

Figure 10:
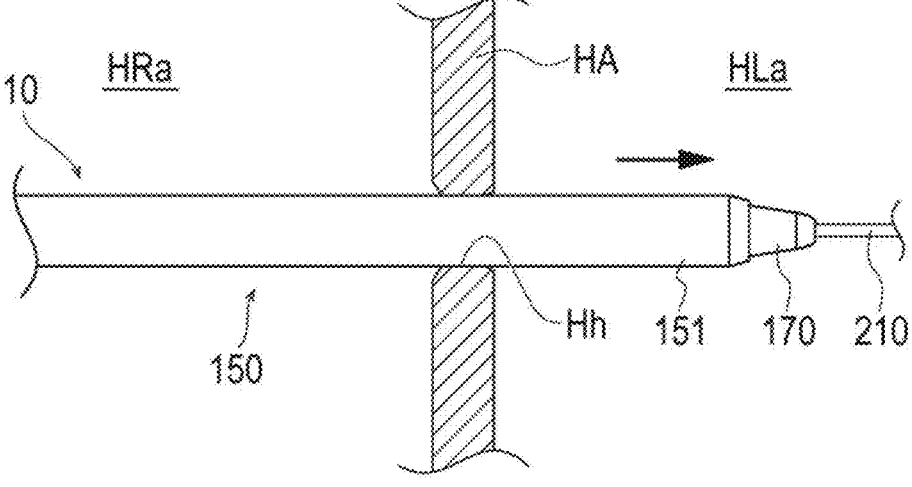
FIG. 10 is a diagram illustrating the treatment method according to the embodiment and is a cross-sectional view schematically illustrating a process of inserting the medical device through the through-hole formed in the atrial septum.

In accordance with an exemplary embodiment, the surgeon delivers the medical device 10 along the guide wire 210 as illustrated in FIG. 10. At this time, the surgeon inserts the distal side of the medical device 10 (distal side of the shaft portion 150) through the through-hole Hh. The through-hole Hh can be widened by the medical device 10 being inserted.

Figure 11:
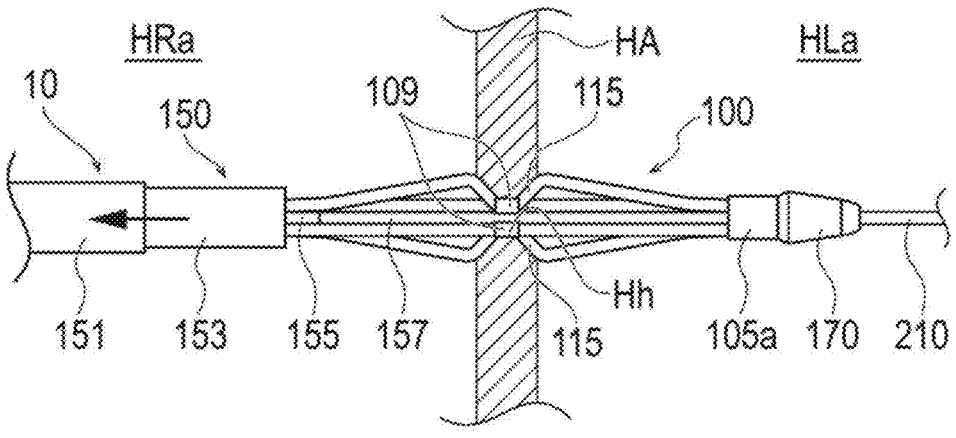
FIG. 11 is a diagram illustrating the treatment method according to the embodiment and is a cross-sectional view schematically illustrating a process of disposing the expansion body of the medical device in the through-hole formed in the atrial septum.

As illustrated in FIG. 11, the surgeon exposes the expansion body 100 by retracting the storage sheath 151 after inserting the medical device 10 through the through-hole Hh. The expansion body 100 is disposed so as to extend in a direction substantially orthogonal to the opening direction of the through-hole Hh (up-down direction in the drawing). At this time, the concave portion 115 of each of the expansion portions 110, 120, 130, and 140 included in the expansion body 100 is disposed inside the through-hole Hh.

Next, the surgeon performs the process (S13) of expanding the through-hole Hh.

Figure 12:
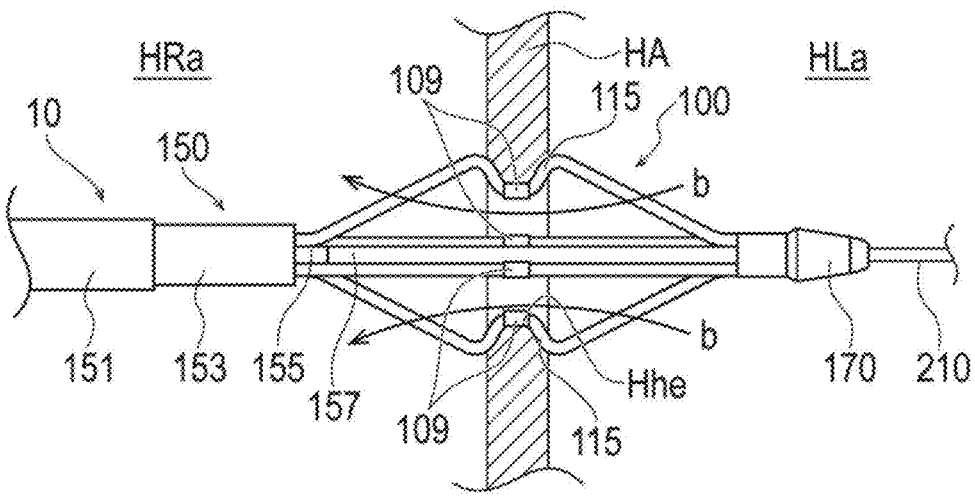
FIG. 12 is a diagram illustrating the treatment method according to the embodiment and is a cross-sectional view schematically illustrating a process of expanding the through-hole formed in the atrial septum.

As illustrated in FIG. 12, the surgeon expands the expansion body 100 in a state where the expansion body 100 is disposed inside the through-hole Hh. The expansion body 100 widens the through-hole Hh so as to exceed the diameter of the dilator 220*b* or the diameter of the storage sheath 151 as the expansion body 100 is expanded to deform. During the expansion of the expansion body 100, each of the expansion portions 110, 120, 130, and 140 comes into contact with four points of the edge portion Hhe of the through-hole Hh. Accordingly, the through-hole Hh is widened such that the shape of the through-hole Hh forms a substantially polygonal shape (quadrangular shape in the illustrated example) in the plan view illustrated in FIG. 16. In the process (S13) of expanding the through-hole Hh, the expansion and contraction of the expansion body 100 may be repeated once or a plurality of times in a state where the expansion body 100 is disposed inside the through-hole Hh. By the expansion and contraction of the expansion body 100 being repeated, the biological tissue of the atrial septum HA around the edge portion Hhe of the through-hole Hh is loosened and becomes likely to be elastically deformed. As a result, the surgeon can more accurately expand the through-hole Hh to a desired size during the treatment using the expansion body 100. As illustrated in FIG. 15, the maintenance treatment element 109 included in each of the expansion portions 110, 120, 130, and 140 satisfactorily maintains contact with the edge portion Hhe of the through-hole Hh contained inside the concave portion 115 (biological tissue in the vicinity of the edge portion Hhe) before and after the expansion of the expansion body 100.

During the expansion of the expansion body 100, the blood flow from the left atrium HLa toward the right atrium HRa is maintained via the circulation portion 108 formed in the expansion body 100. As for the patient suffering from the chronic heart failure attributable to the enlargement of the myocardium of the left ventricle HLw, the left atrium HLa becomes higher in blood pressure than the right atrium HRa, and thus the blood that passes through the through-hole Hh flows from the left atrium HLa toward the right atrium HRa.

Next, the surgeon performs the process (S14) of confirming the hemodynamics in the vicinity of the through-hole Hh.

As illustrated in FIG. 8, the surgeon delivers a hemodynamic confirmation device 240 to the right atrium HRa via, for example, the inferior vena cava Iv. A known echo catheter, for example, can be used as the hemodynamic confirmation device 240. The surgeon can cause a display apparatus such as a display to display an echo image acquired by the hemodynamic confirmation device 240 and confirm the rate of the blood flow through the through-hole Hh based on the result of the display. Note that the process of confirming the hemodynamics may be started at any of timings before, during, and after the expansion of the through-hole Hh. In addition, the process of confirming the hemodynamics may be ended at any timing following the expansion of the through-hole Hh by the expansion body 100.

By performing the process described above, the surgeon can confirm whether or not the hemodynamics is an assumed one (i.e., whether or not the rate of the blood flow from the left atrium HLa to the right atrium HRa is at a desired rate). In a case where the surgeon determines based on the result of the hemodynamic confirmation that the blood flow rate is less than the desired rate, the surgeon can increase the amount of expansion of the expansion body 100. The increase in the amount of expansion of the expansion body 100 can be because the post-maintenance treatment blood flow rate to be described later may become insufficient. In contrast, in a case where the surgeon determines based on the result of the hemodynamic confirmation that the blood flow rate exceeds the desired rate, the surgeon can decrease the amount of expansion of the expansion body 100. The decrease in the amount of expansion of the expansion body can be because the post-maintenance treatment blood flow rate may excessively increase.

In addition, the surgeon can, for example, expand the expansion body 100 by a relatively small amount of expansion, confirm the hemodynamics, and then increase the amount of expansion of the expansion body 100 in stages. By increasing the size of the through-hole Hh in stages, it is possible to prevent a sudden and significant deformation of the through-hole Hh. As a result, the relative burden on the atrial septum HA can be reduced. Further, the biological tissue in the vicinity of the through-hole Hh of the atrial septum HA can be prevented from undergoing, for example, an injury such as tearing. Note that the process of confirming the hemodynamics can be appropriately performed every time the expansion process is finished.

In addition, the surgeon can, for example, expand the expansion body 100 by a relatively large amount of expansion, confirm the hemodynamics, and then decrease the amount of expansion of the expansion body 100 in stages. By expanding the through-hole Hh so as to become relatively large in the early stage of the expansion as described above, a post-maintenance treatment contraction of the through-hole Hh attributable to an elastic biological tissue deformation can be suitably suppressed.

Next, the surgeon performs the process (S15) of performing the maintenance treatment for maintaining the size of the through-hole Hh.

As illustrated in FIGS. 13 and 15, the surgeon cauterizes the edge portion Hhe of the through-hole Hh with high-frequency energy (heating cauterization) by imparting the high-frequency energy to the edge portion Hhe of the through-hole Hh through the maintenance treatment element 109 in a state where the maintenance treatment element 109 disposed in the concave portion 115 of the expansion body 100 is disposed in the vicinity of the edge portion Hhe of the through-hole Hh. During the cauterization through the maintenance treatment element 109, the contact between the maintenance treatment element 109 disposed in the concave portion 115 and the edge portion Hhe of the through-hole Hh is maintained relatively well. When the biological tissue in the vicinity of the edge portion Hhe of the through-hole Hh is cauterized through the maintenance treatment element 109, a denatured portion Hd in which the biological tissue is denatured is formed in the vicinity of the edge portion Hhe. The biological tissue in the denatured portion Hd loses elasticity, and thus the through-hole Hh is capable of maintaining the shape at a time when the through-hole Hh is widened by the expansion body 100.

Figure 16:
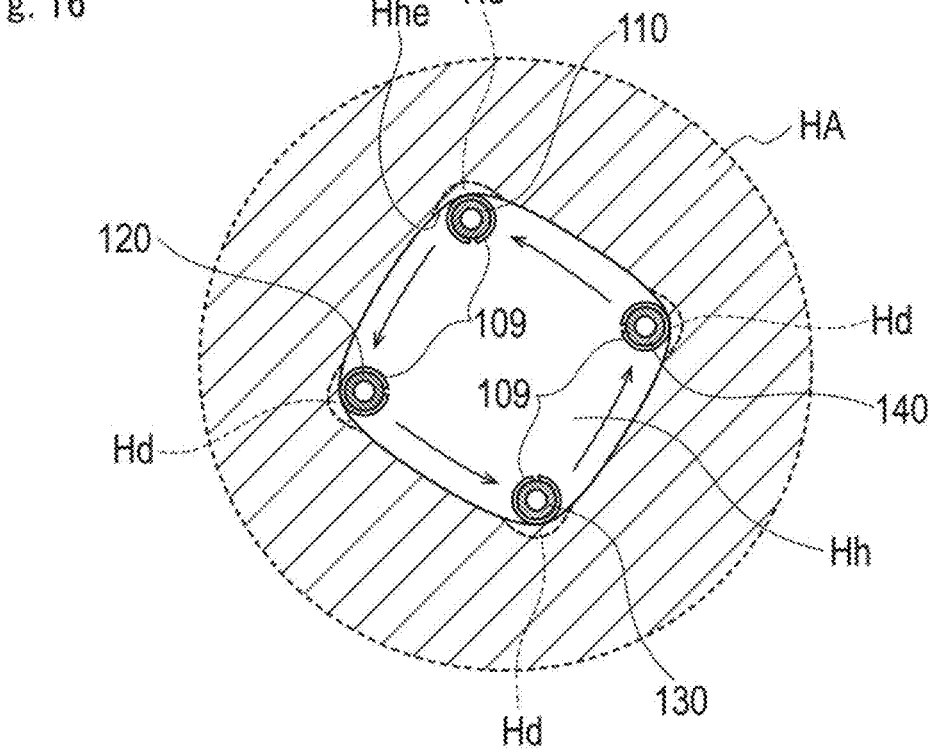
FIG. 16 is a front view of the through-hole viewed from the arrow XVIA direction illustrated in FIG. 13.

When heat is imparted from the maintenance treatment element 109 to the edge portion Hhe of the through-hole Hh, each of the expansion portions 110, 120, 130, and 140 comes into contact with the edge portion Hhe and maintains a widened state. Accordingly, the through-hole Hh has a substantially polygonal shape in plan view after the maintenance treatment as illustrated in FIG. 16. In addition, the part excluding the part where the denatured portion Hd is formed by the heat being imparted by the maintenance treatment element 109 (part extending substantially linearly between the denatured portions Hd in the plan view illustrated in FIG. 16) is affected little by the heat imparted from the maintenance treatment element 109, and thus the degree of cauterization (degree of denaturation) is smaller at the part than in the denatured portion Hd. In accordance with an exemplary embodiment, it is possible to prevent thrombus generation around the through-hole Hh by a plurality of locations being locally cauterized without cauterization over the entire circumference of the edge portion Hhe of the through-hole Hh as described above.

Note that the maintenance treatment may be performed while, for example, the expansion body 100 is expanded. In addition, the maintenance treatment may be performed while, for example, the expansion body 100 is rotated (see the arrows illustrated in FIG. 16). At this time, the direction of rotation of the expansion body 100 is not particularly limited.

After the cauterization by means of the maintenance treatment element 109 is performed, the periphery of the edge portion Hhe of the through-hole Hh is cooled relatively quickly by the blood that passes through the through-hole Hh. Accordingly, it is possible to inhibit the effect of the heat imparted from the maintenance treatment element 109 from spreading around the denatured portion Hd.

The maintenance treatment is not limited to the heating by means of the maintenance treatment element 109 (heating by means of high-frequency energy). The maintenance treatment can be performed by, for example, a method for performing heating or cooling by means of microwave energy, ultrasound energy, coherent light such as laser, a heated fluid, a cooled fluid, or a chemical medium, a method using a heater provided with an electric wire or the like, a frictional heat generation method, a method using an indwelling tool (described later, see FIGS. 26 and 27), a method based on incision (described later, see FIG. 29), or a method in which the methods are combined in any manner.

Next, the surgeon performs the process (S16) of confirming the hemodynamics in the vicinity of the through-hole Hh after the maintenance treatment is performed.

The process of confirming the hemodynamics can be performed by means of the hemodynamic confirmation device 240 as described above. The surgeon removes the medical device 10 from the through-hole Hh in a case where the rate of the blood flow through the through-hole Hh is the desired rate as a result of the confirmation of the hemodynamics in the vicinity of the through-hole Hh after the maintenance treatment. In removing the medical device 10, the surgeon stores the expansion body 100 in the storage sheath 151 by contracting the expansion body 100. Subsequently, the medical device 10 is removed from the living body along the guide wire 210.

As illustrated in FIG. 14, the blood flow through the through-hole Hh is suitably maintained even after the medical device 10 is removed from the through-hole Hh. As described above, in the present embodiment, the blood flow dynamics in the vicinity of the through-hole Hh is confirmed before and after the maintenance treatment with respect to the through-hole Hh, and thus the post-treatment blood flow rate can be adjusted to a desired rate. As a result, the rate of the blood flow from the patient's left atrium HLa toward the patient's right atrium HRa becomes appropriate, heart failure treatment effects can be further improved, and the patient's post-treatment burden can be reduced.

The surgeon can, for example, expand the through-hole Hh again or perform the maintenance treatment with respect to the through-hole Hh again in a case where the blood flow rate is lower than the desired rate as a result of the confirmation of the hemodynamics in the vicinity of the through-hole Hh after the maintenance treatment. By performing these treatments again, the size of the through-hole Hh can be adjusted such that the blood flow rate in the through-hole Hh reaches the desired rate. Note that the hemodynamic confirmation, the maintenance treatment, and the expansion of the through-hole Hh can be performed with the expansion body 100 disposed in the through-hole Hh during the treatment by means of the medical device 10 according to the present embodiment, and thus each of the work processes described above can be, for example, performed at any timing without the medical device 10 being replaced. By performing the processes in combination, the surgeon can more accurately adjust the size of the through-hole Hh such that desired hemodynamics can be realized.

For example, in a case where the maintenance treatment is performed again, it is also possible to rotate the expansion body 100 and dispose the maintenance treatment element 109 in a displaced manner such that the denatured portion Hd is formed at a different site. By performing the treatment in this manner, it is possible to form the denatured portion Hd at a different position in the edge portion Hhe of the through-hole Hh, and thus the post-maintenance treatment shape of the through-hole Hh can be more suitably maintained. In addition, for example, the temperature that is imparted by the maintenance treatment element 109 can be changed for each of the expansion portions 110, 120, 130, and 140 or the temperature that is imparted by the maintenance treatment element 109 can be changed every time the maintenance treatment is performed.

As described above, the treatment method according to the present embodiment includes (i) an expansion process of expanding the through-hole Hh formed in the atrial septum HA such that the right atrium HRa and the left atrium HLa of a heart failure patient communicate with each other, (ii) a confirmation process of confirming the hemodynamics in the vicinity of the through-hole Hh, (iii) a process of performing the maintenance treatment for maintaining the size of the through-hole Hh, and (iv) a confirmation process of confirming the hemodynamics in the vicinity of the through-hole Hh after the maintenance treatment.

Next, the action of the present embodiment will be described.

The medical device 10 according to the present embodiment includes the shaft portion 150, the expandable and contractible expansion body 100 provided on the distal side of the shaft portion 150, and the maintenance treatment element 109 disposed in the expansion body 100 and imparting energy to biological tissue. The expansion body 100 that is expanded and deformed includes the concave portion 115 recessed in a direction intersecting with the axial direction of the shaft portion 150. The maintenance treatment element 109 is disposed in the concave portion 115.

In accordance with an exemplary embodiment, the medical device 10 is capable of preventing the maintenance treatment element 109 disposed in the concave portion 115 from being displaced from a treatment target site by the concave portion 115 formed when the expansion body 100 is expanded to deform being disposed at the treatment target site (such as the edge portion Hhe of the through-hole Hh formed in the atrial septum HA). As a result, a surgeon using the medical device 10 can perform an appropriate treatment by means of the maintenance treatment element 109.

In addition, the expansion body 100 included in the medical device 10 includes the circulation portion 108 allowing blood flow via the through-hole Hh in a state where the concave portion 115 is disposed in the through-hole Hh formed in the atrial septum HA of a patient.

With the medical device 10 described above, a surgeon can dispose the expansion body 100 in the through-hole Hh and help prevent the blood flow through the through-hole Hh from being suppressed during, for example, the expansion by means of the expansion body 100 or the treatment by means of the maintenance treatment element 109. Accordingly, the relative burden on the patient's body attributable to blocking of the through-hole Hh can be reduced. In addition, the surgeon can confirm the blood flow dynamics in the vicinity of the through-hole Hh in a state where the expansion body 100 is disposed in the through-hole Hh, and thus the size of the through-hole Hh can be appropriately adjusted.

In addition, the expansion body 100 included in the medical device 10 has the concave portions 115 at a plurality of different positions in the circumferential direction of the expansion body 100 in the expanded and deformed state and the maintenance treatment element 109 is disposed in each of the plurality of concave portions 115.

With the medical device 10, the surgeon can simultaneously impart heat to the biological tissue as a treatment target site from the maintenance treatment element 109 disposed in each of the plurality of concave portions 115 included in the expansion body 100, and thus the surgeon can perform his or her procedure with relative efficiency. In addition, each of the plurality of concave portions 115 included in the expansion body 100 is suitably positioned with respect to the treatment target site. Accordingly, treatment can be more reliably performed on a desired site even in a case where heat is simultaneously imparted to a plurality of locations.

In addition, the linear member shaped in advance so as to form the concave portion 115 when expanded to deform constitutes the expansion body 100 included in the medical device 10.

With the medical device 10, the surgeon can form the concave portion 115 in the expansion body 100 by expanding and deforming the expansion body 100. Accordingly, the surgeon can rather smoothly and easily perform the treatment by means of the expansion body 100.

In addition, the concave portion 115 of the expansion body 100 includes the bottom portion 115a, the distal side standing portion 115b formed on the distal side in the axial direction as compared with the bottom portion 115a and rising in a direction intersecting with the axial direction from the bottom portion 115a, and the proximal side standing portion 115c formed on the proximal side in the axial direction as compared with the bottom portion 115a and rising in a direction intersecting with the axial direction from the bottom portion 115a. In accordance with an exemplary embodiment, the maintenance treatment element 109 is disposed in the bottom portion 115a of the concave portion 115.

With the medical device 10, the maintenance treatment element 109 disposed in the bottom portion 115a of the concave portion 115 can be more reliably brought into contact with the treatment target site and the surgeon can rather smoothly perform the procedure by the expansion body 100 being disposed such that the concave portion 115 contains the treatment target site (such as the edge portion Hhe of the through-hole Hh formed in the atrial septum HA).

In addition, the shaft portion 150 of the medical device 10 includes the storage sheath 151 capable of storing the expansion body 100 that is contracted and the distal tip 170 disposed on the distal side of the storage sheath 151 and having an outer diameter decreasing toward the distal side. In accordance with an exemplary embodiment, the expansion body 100 is configured to be expandable and deformable in a state of being exposed from the storage sheath 151 and disposed between the storage sheath 151 and the distal tip 170.

With the medical device 10, the surgeon can store the expansion body 100 that is contracted in the storage sheath 151 until the expansion body 100 is delivered to the treatment target site (such as the edge portion Hhe of the through-hole Hh formed in the atrial septum HA), and thus the delivery work can be rather smoothly performed. In accordance with an exemplary embodiment, the surgeon can rather easily position the expansion body 100 with respect to the treatment target site by delivering the expansion body 100 to the treatment target site and exposing the expansion body 100 from the storage sheath 151 in a state where the distal tip 170 is disposed on the back side (distal side) as compared with the treatment target site. Further, the surgeon can position the maintenance treatment element 109 disposed in the concave portion 115 of the expansion body 100 at the treatment target site by expanding the expansion body 100 in a state where the expansion body 100 is positioned at the treatment target site.

In addition, the treatment method according to the present embodiment includes the expansion process of expanding the through-hole Hh formed in the atrial septum HA such that the right atrium HRa and the left atrium HLa of a heart failure patient communicate with each other, the confirmation process of confirming the hemodynamics in the vicinity of the through-hole Hh, and the process of performing the maintenance treatment for maintaining the size of the through-hole Hh.

By the treatment method, a surgeon can obtain a determination index during his or her procedure as to whether or not the through-hole Hh is formed in a desired size by confirming the hemodynamics in the vicinity of the through-hole Hh formed in the atrial septum HA. As a result, the surgeon can improve the therapeutic effect of heart failure treatment.

Next, a treatment method according to a modification example will be described.

Figure 17:
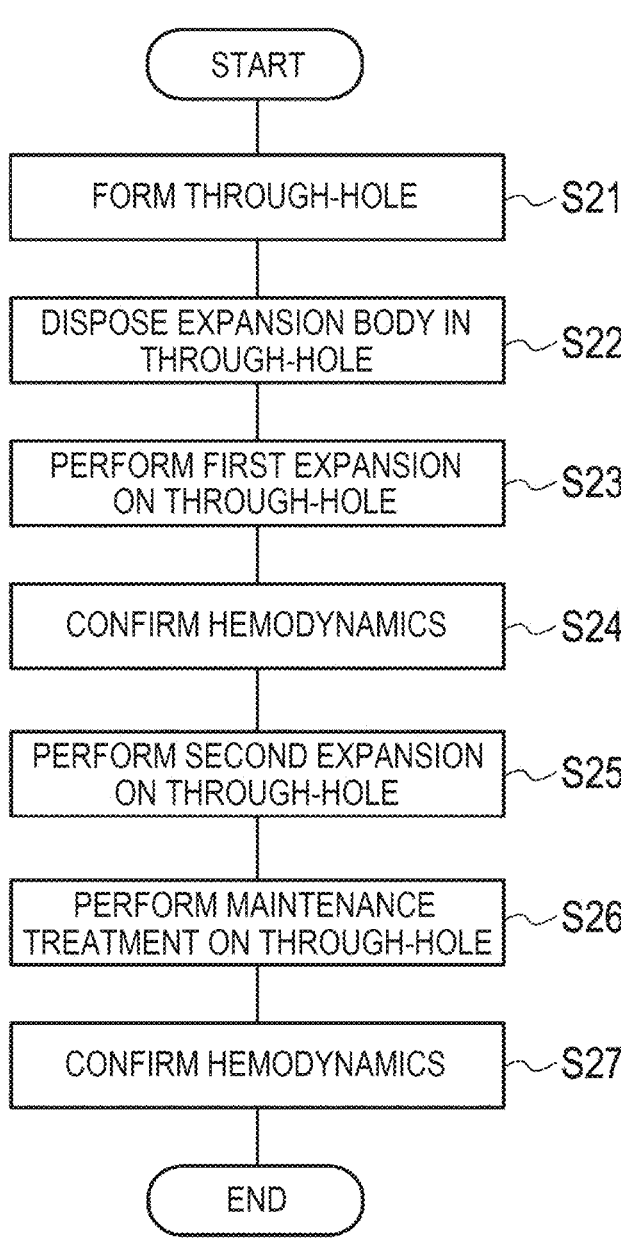
FIG. 17 is a flowchart illustrating the procedure of a treatment method according to a modification example.

As illustrated in FIG. 17, the treatment method according to the modification example includes a first expansion process (S23) and a second expansion process (S25) as through-hole expansion processes. The processes other than the processes (S23 and S25) are respectively and substantially the same as the processes described in the above-described embodiment and thus will not be described. In addition, unless otherwise noted, it is assumed that the processes can be performed in the same procedure as in the above description. Note that a hemodynamic confirmation process (S24) can be omitted as appropriate in the present modification example.

Figure 18:
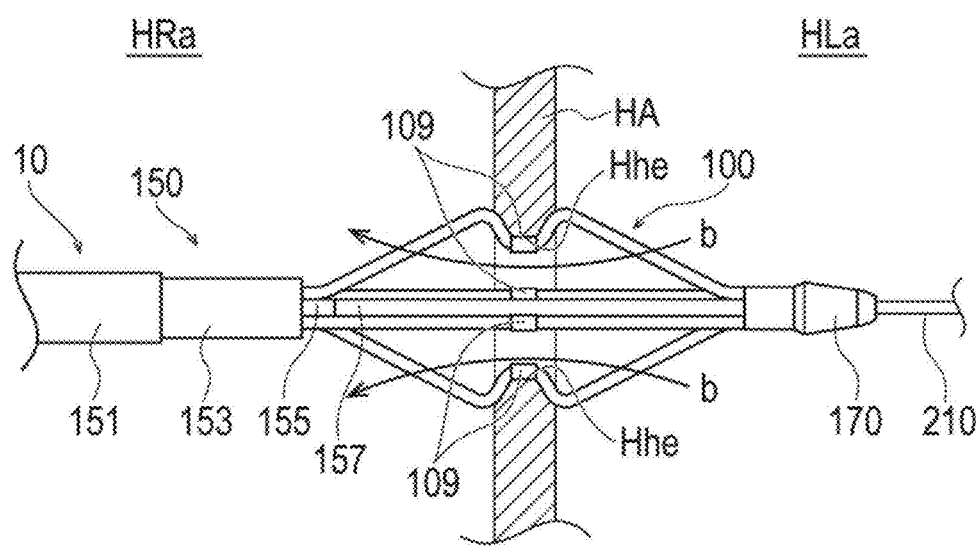
FIG. 18 is a diagram illustrating the treatment method according to the modification example and is a cross-sectional view schematically illustrating a process of expanding the through-hole formed in the atrial septum (first expansion process).

As illustrated in FIG. 18, in the first expansion process (preliminary expansion process), a surgeon expands the expansion body 100 by a predetermined amount of expansion with the expansion body 100 disposed in the through-hole Hh. The surgeon confirms the hemodynamics in the vicinity of the through-hole Hh with the expansion body 100 expanded. At this time, the surgeon confirms whether or not the hemodynamics has a desired magnitude. As a result, the surgeon can obtain a determination index as to how much he or she should expand the expansion body 100 and the through-hole Hh in the following second expansion process (overexpansion process).

Figure 19:
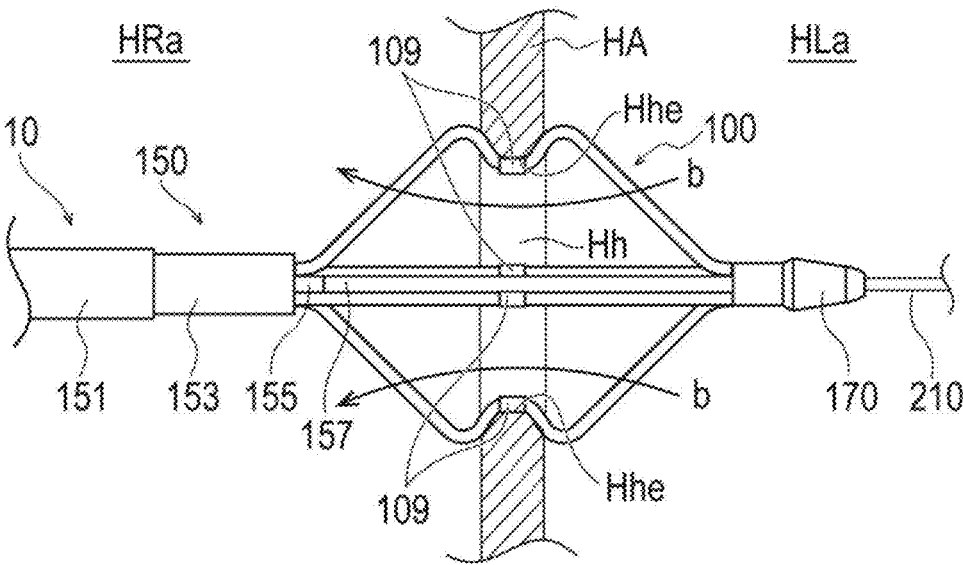
FIG. 19 is a diagram illustrating the treatment method according to the modification example and is a cross-sectional view schematically illustrating a process of expanding the through-hole formed in the atrial septum (second expansion process).

Next, the surgeon performs the second expansion process as illustrated in FIG. 19. In the second expansion process, the expansion body 100 is expanded such that the amount of expansion becomes larger than when the expansion body 100 is expanded in the first expansion process. The standard of the expansion amount of the expansion body 100 is adjusted to a size that assumes the amount by which the through-hole Hh contracts due to the elastic deformation of biological tissue after the next process (S26) of performing maintenance treatment. Specifically, in the second expansion process, the amount of contraction at a time when membranous tissue such as the atrial septum is expanded (physically widened) is assumed and the expansion amount (expansion diameter) of the expansion body 100 is set such that the size (inner diameter) of the through-hole Hh is substantially the same as the size at the time of the expansion in the first expansion process after the maintenance treatment is finished.

Figure 20:
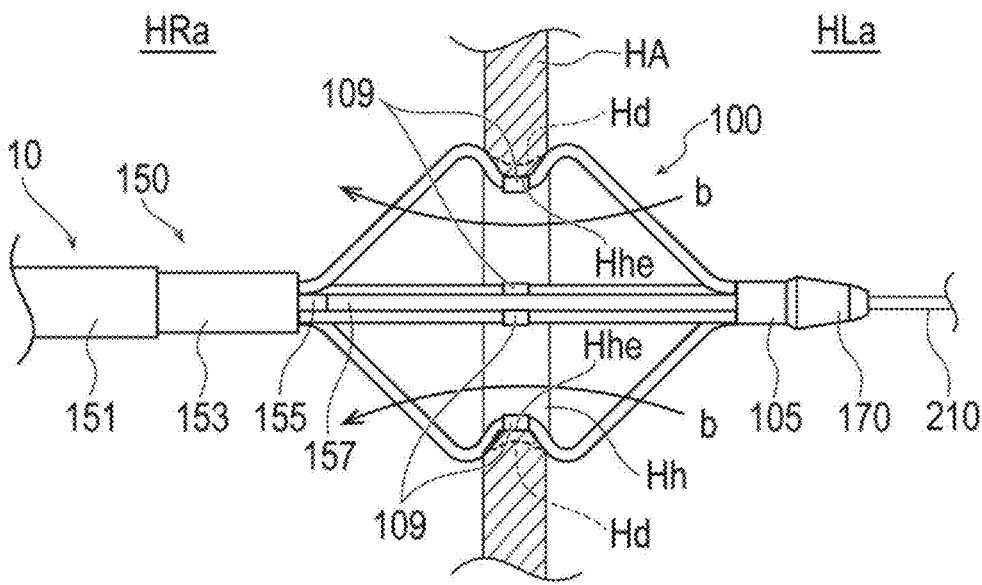
FIG. 20 is a diagram illustrating the treatment method according to the modification example and is a cross-sectional view schematically illustrating a process of performing the maintenance treatment on the through-hole formed in the atrial septum.
Figure 21:
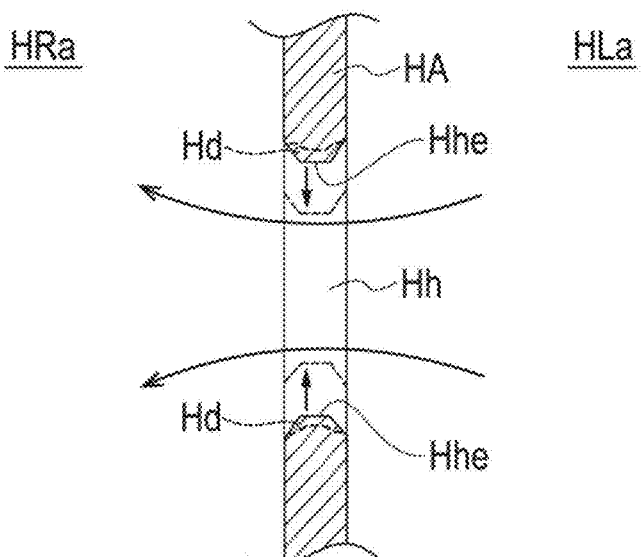
FIG. 21 is a diagram illustrating the treatment method according to the modification example and is a cross-sectional view schematically illustrating a state after the expansion body of the medical device is removed from the through-hole formed in the atrial septum.

After performing the second expansion process, the surgeon performs the maintenance treatment as illustrated in FIG. 20. As in the case of the embodiment described above, the denatured portion Hd is formed in the edge portion Hhe of the through-hole Hh by the maintenance treatment being performed. After performing the maintenance treatment, the expansion body 100 is removed from the through-hole Hh as illustrated in FIG. 21. When the expansion body 100 is removed from the through-hole Hh, the through-hole Hh contracts due to the elastic deformation of the biological tissue. The size of the through-hole Hh becomes substantially the same as the size at the time of the expansion in the first expansion process.

Next, the surgeon confirms the hemodynamics in the vicinity of the through-hole Hh and confirms whether or not the flow rate of the blood that flows from the left atrium HLa to the right atrium HRa is at a desired blood flow rate.

As described above, in the treatment method according to the present modification example, the overexpansion process by means of the expansion body 100 is performed before the maintenance treatment is performed, and thus it is possible to suppress a decrease in blood flow rate entailed by an elastic biological tissue contraction. Accordingly, hemodynamics substantially the same as the hemodynamics confirmed in the first expansion process is maintained even after the expansion body 100 is removed from the through-hole Hh. Accordingly, the flow rate of the blood from the left atrium HLa toward the right atrium HRa of a patient becomes appropriate, heart failure treatment effects can be further improved, and the patient's post-treatment burden can be reduced.

Note that it is possible to perform the maintenance treatment while, for example, overexpanding the expansion body 100 in the treatment method according to the modification example. In addition, it is possible to perform the maintenance treatment while, for example, rotating the expansion body 100. In addition, it is possible to overexpand the expansion body 100 again after the maintenance treatment and subsequently re-perform the maintenance treatment. At this time, the surgeon may perform the maintenance treatment at a position different from the position where the denatured portion Hd is already formed by rotating the expansion body 100 and adjusting the position of the maintenance treatment element 109. In addition, the rotation of the expansion body 100, the overexpansion of the expansion body 100, the maintenance treatment, and the like can be, for example, performed a plurality of times in this order and with this order appropriately changed.

As described above, the treatment method according to the present modification example includes (i) the first expansion process of expanding the through-hole Hh formed in the atrial septum HA such that the right atrium HRa and the left atrium HLa of a heart failure patient communicate with each other, (ii) the second expansion process of expanding the through-hole Hh more than in the first expansion process (increasing the expansion diameter), and (iii) the process of performing the maintenance treatment on the through-hole Hh after the second expansion process.

Next, a medical device according to a modification example and another treatment method will be described. Note that treatment using each device and member described below can be appropriately incorporated into each treatment method described above (FIGS. 6 and 17) and can be appropriately replaced with each corresponding treatment.

Figure 22:
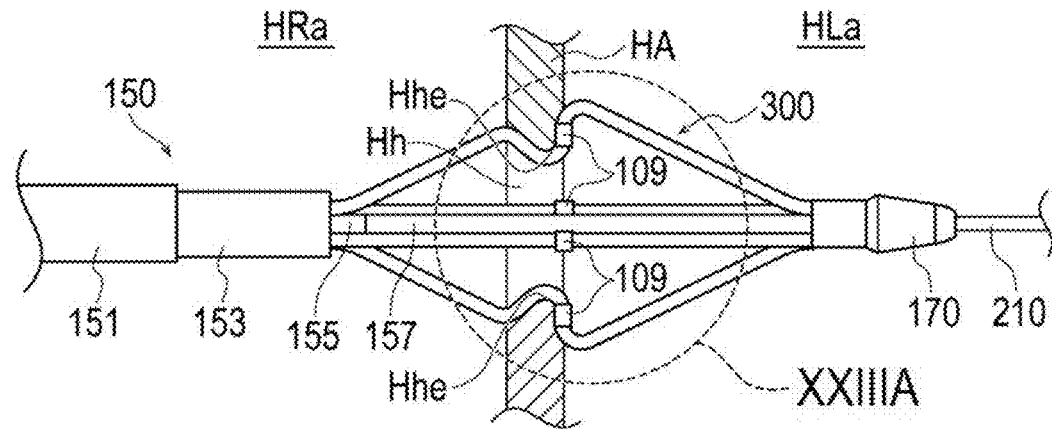
FIG. 22 is a cross-sectional view illustrating a medical device according to Modification Example 1.
Figure 23:
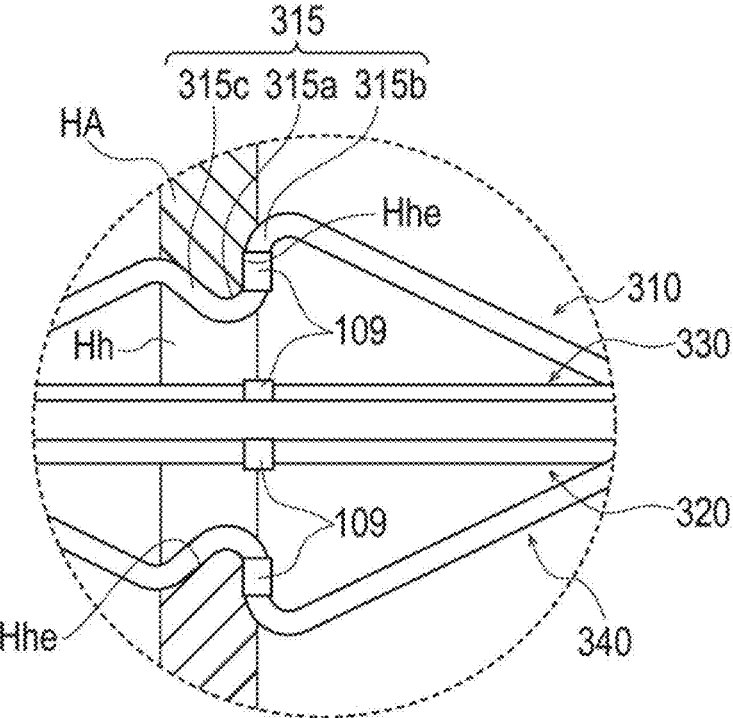
FIG. 23 is an enlarged view illustrating the broken line portion XXIIIA part illustrated in FIG. 22.

A medical device according to Modification Example 1 is illustrated in FIGS. 22 and 23.

As illustrated in FIGS. 22 and 23, in the medical device according to the present modification example, the maintenance treatment element 109 is disposed in a distal side standing portion 315*b* included in a concave portion 315 of an expansion body 300. Note that the maintenance treatment element 109 is also disposed in the distal side standing portion 315*b* of the concave portion 315 of each of expansion portions 320, 330, and 340 other than a first expansion portion 310 of the expansion body 300 although this is illustrated in a simplified manner in FIGS. 22 and 23.

The distal side standing portion 315*b* is formed so as to have a dimension in the height direction (dimension in the up-down direction in FIG. 23) larger than the height-direction dimension of a proximal side standing portion 315*c*. A bottom portion 315*a* extends between the distal side standing portion 315*b* and the proximal side standing portion 315*c*.

As illustrated in FIG. 23, when maintenance treatment is performed with respect to the through-hole Hh, the maintenance treatment element 109 is disposed with respect to the edge portion Hhe of the through-hole Hh (edge portion on the distal side in the insertion direction of the expansion body 100). During the disposition, a surgeon can dispose the maintenance treatment element 109 in the edge portion Hhe of the through-hole Hh by, for example, moving the expansion body 100 to the proximal side (left side in the drawing) after temporarily disposing the maintenance treatment element 109 disposed in the concave portion 315 on the distal side as compared with the through-hole Hh (right side in the drawing).

In accordance with an exemplary embodiment, it can be possible to increase the contact area between the maintenance treatment element 109 and the edge portion Hhe of the through-hole Hh by disposing the maintenance treatment element 109 in the distal side standing portion 315*b* of the concave portion 315 as illustrated in the present modification example. Accordingly, the post-maintenance treatment size of the through-hole Hh can be suitably maintained.

Note that the maintenance treatment element 109 can be disposed in, for example, the proximal side standing portion 315*c*. In this case, the proximal side standing portion 315*c* can be formed so as to have, for example, a dimension in the height direction (dimension in the up-down direction in FIG. 23) larger than the height-direction dimension of the distal side standing portion 315*b*. In addition, when the maintenance treatment element 109 is disposed in the edge portion Hhe of the through-hole Hh in the case of this configuration, the surgeon can dispose the maintenance treatment element 109 in the edge portion Hhe of the through-hole Hh by, for example, moving the expansion body 100 to the distal side (right side in the drawing) after temporarily disposing the maintenance treatment element 109 disposed in the concave portion 315 on the proximal side as compared with the through-hole Hh (left side in the drawing).

Note that the position described in relation to the expansion body 100 (see FIG. 15) according to the above-described embodiment, the above-described position of disposition in the distal side standing portion 315b or the proximal side standing portion 315c, and the like can be appropriately combined as to the disposition of the maintenance treatment element 109. For example, in a case where the expansion body is provided with a plurality of expansion portions, one expansion body can be formed by appropriately combining the disposition forms described above.

Figure 24:
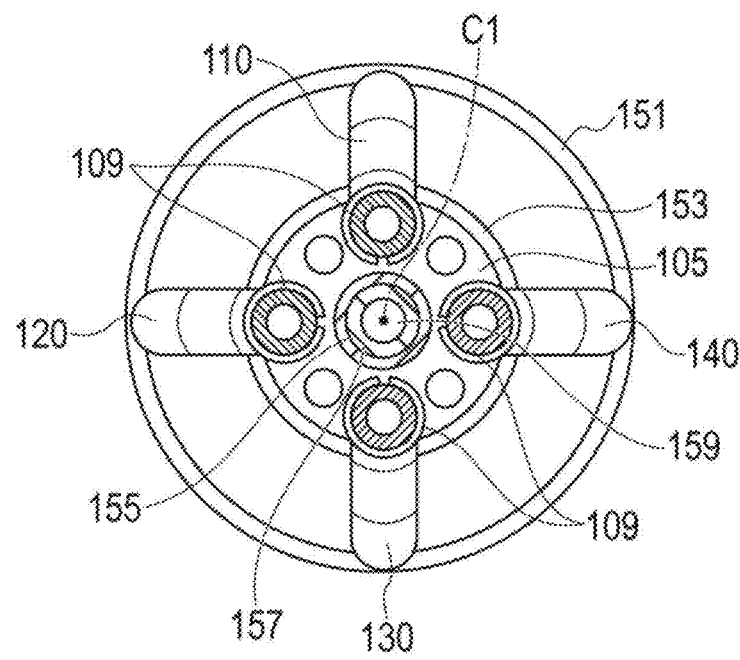
FIG. 24 is a front view of the distal portion of a medical device according to Modification Example 2 and is a diagram illustrating a state where an expansion body is stored in a storage sheath.
Figure 25:
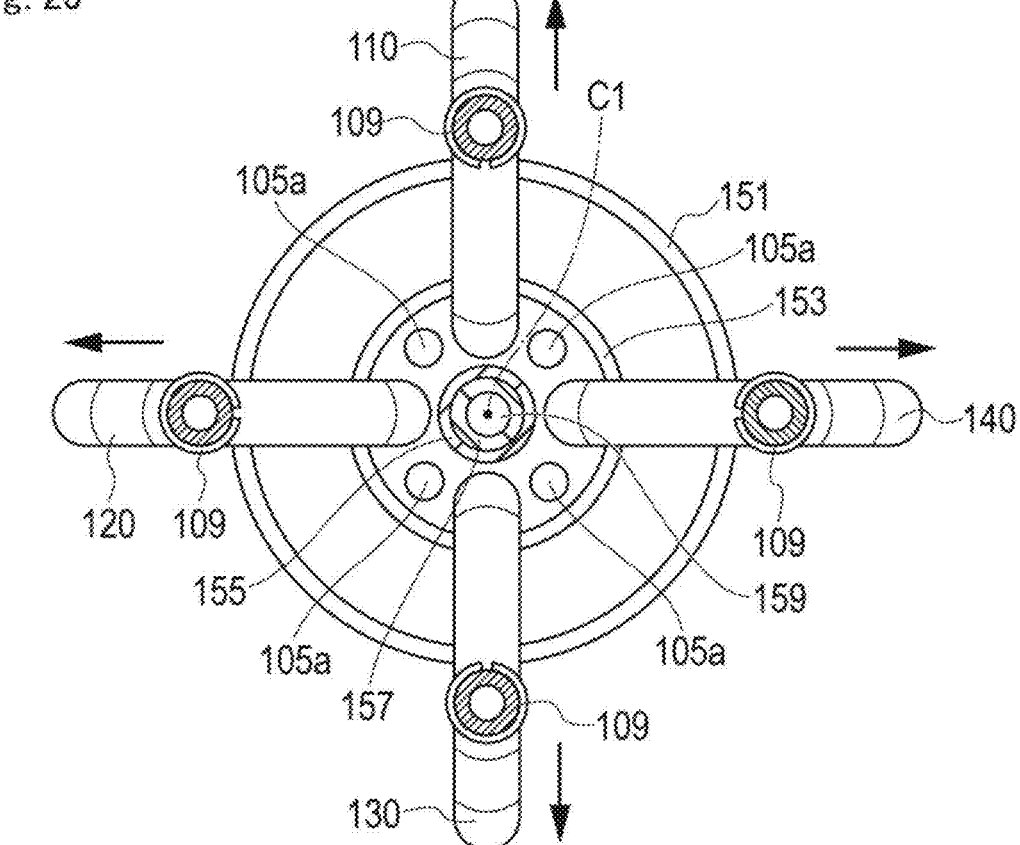
FIG. 25 is a front view of the distal portion of the medical device according to Modification Example 2 and is a diagram illustrating a state where the expansion body is exposed from the storage sheath.

A medical device according to Modification Example 2 is illustrated in FIGS. 24 and 25.

In the medical device 10 according to the above-described embodiment, each of the expansion portions 110, 120, 130, and 140 is disposed so as not to overlap the central axis C1 of the shaft portion 150 in the up-down direction and the left-right direction when viewed from the front (see FIGS. 4 and 5). In contrast, in the present modification example, each of the expansion portions 110, 120, 130, and 140 is disposed such that the expansion portions that face each other overlap in the up-down direction or the left-right direction when viewed from the front. Even in a case where each of the expansion portions 110, 120, 130, and 140 is disposed in this manner, treatment by means of the expansion body 100 can be performed rather smoothly although it is difficult to reduce the size of the storage sheath 151.

Figure 26:
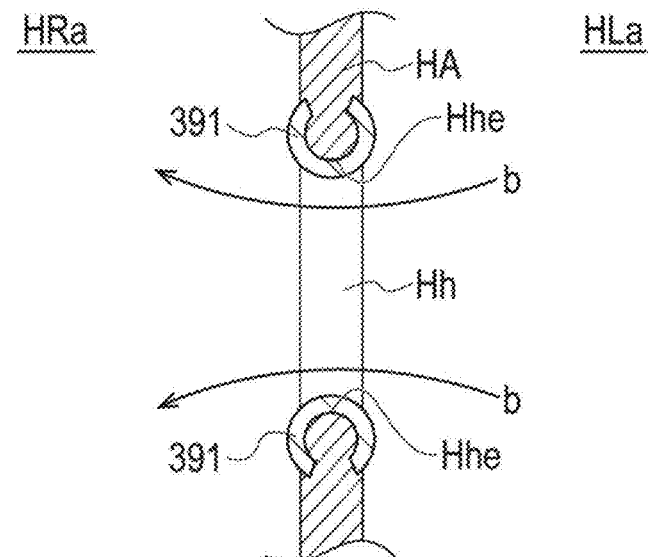
FIG. 26 is a cross-sectional view schematically illustrating an example of maintenance treatment for maintaining the size of the through-hole formed in the atrial septum.
Figure 27:
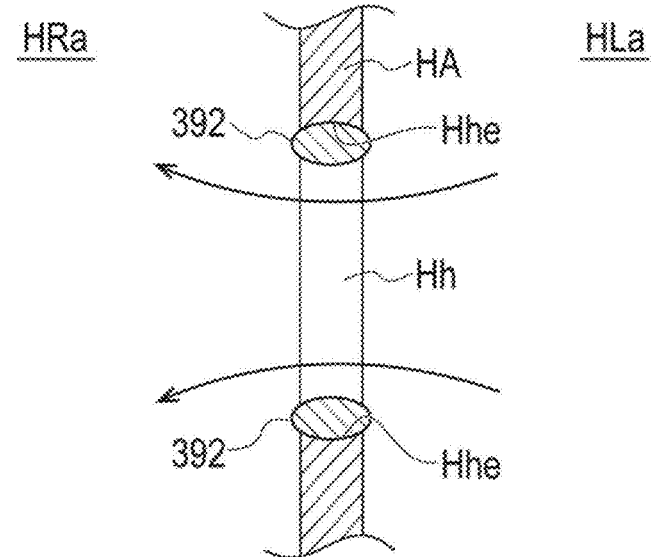
FIG. 27 is a cross-sectional view schematically illustrating an example of the maintenance treatment for maintaining the size of the through-hole formed in the atrial septum.

A modification example of the maintenance treatment is illustrated in FIGS. 26 and 27.

Although the maintenance treatment is performed by a thermal effect being imparted to the biological tissue by the maintenance treatment element 109 disposed in the expansion body 100 and the denatured portion Hd (see FIG. 15) being formed as a result in the embodiment described above, specific methods for the maintenance treatment are not limited insofar as the through-hole Hh can be maintained at a desired size. For example, the size of the through-hole Hh can be maintained by means of a predetermined indwelling object as illustrated in the present modification example.

As illustrated in FIG. 26, during the maintenance treatment, the size of the through-hole Hh can be maintained by a predetermined member 391 being disposed in the edge portion Hhe of the through-hole Hh. In accordance with an exemplary embodiment, for example, a clip-type member made of a biocompatible material, a coil-shaped member, a stent-type member can be inserted into the entire through-hole Hh, or the like can be used as the member 391.

As illustrated in FIG. 27, in another example of the maintenance treatment, the size of the through-hole Hh may be maintained by materials 392 such as an adhesive and gel made of a biodegradable material being disposed in the edge portion Hhe of the through-hole Hh. Note that a known biodegradable material can be used as the biodegradable material. In addition, the size of the through-hole Hh may be maintained by, for example, the edge portion Hhe of the through-hole Hh being sutured by means of a suture thread made of a biocompatible or biodegradable material.

Note that the member 391 indwelled so that the size of the through-hole Hh is maintained, the various materials 392 indwelled in the edge portion Hhe of the through-hole Hh, and the like can be, for example, mounted in the concave portion 115 (see FIG. 2) of the expansion body 100 and delivered to the through-hole Hh.

Figure 28:
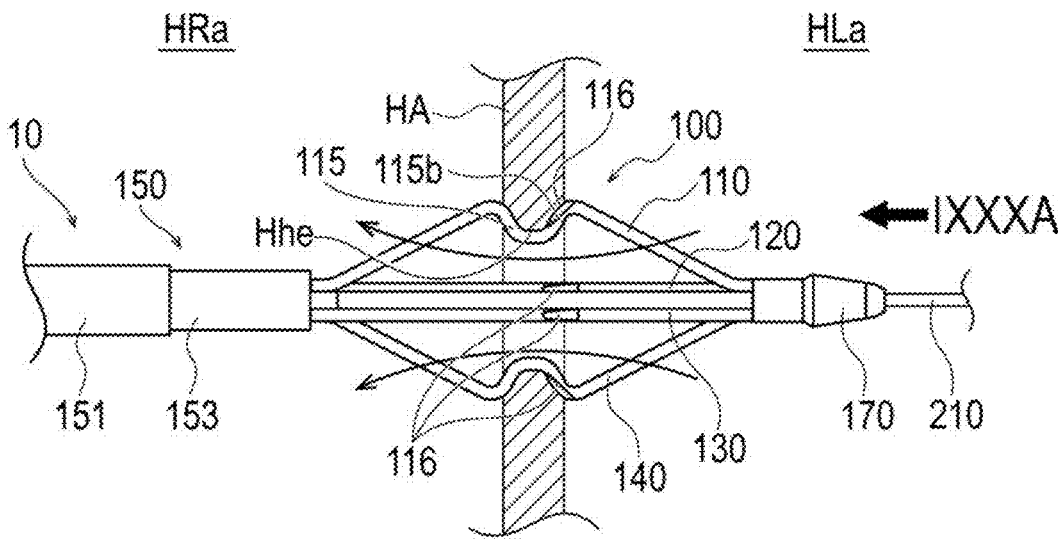
FIG. 28 is a cross-sectional view schematically illustrating an example of the maintenance treatment for maintaining the size of the through-hole formed in the atrial septum.
Figure 29:
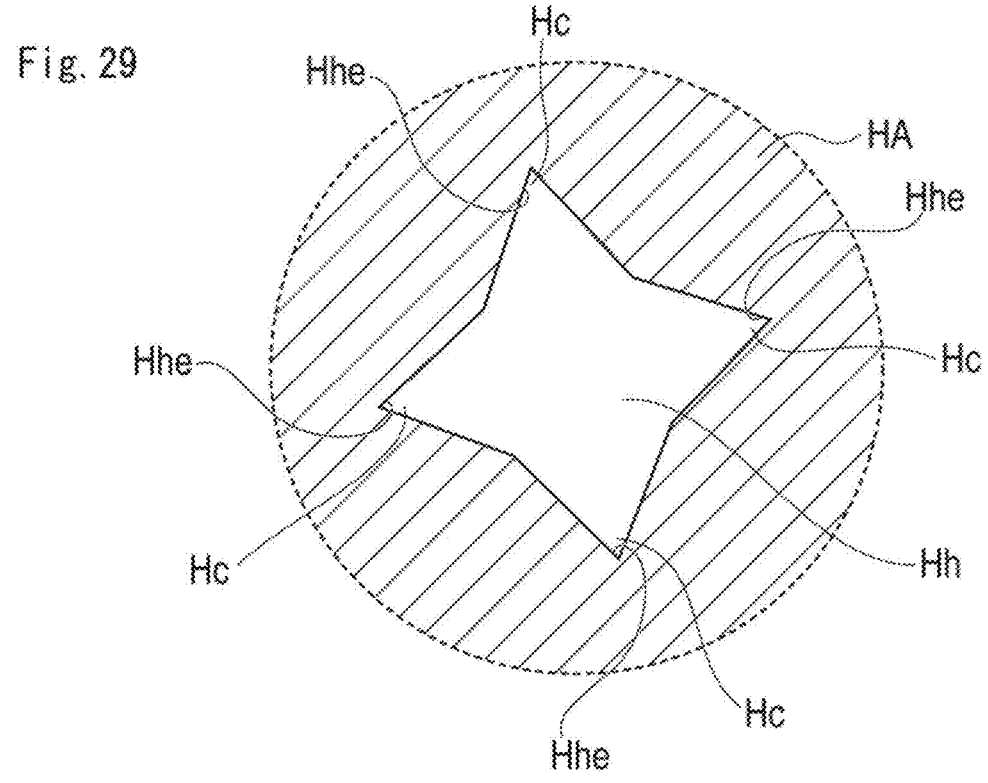
FIG. 29 is a front view of the through-hole viewed from the arrow IXXXA direction illustrated in FIG. 28.

In addition, as illustrated in FIGS. 28 and 29, the maintenance treatment can be performed by means of, for example, the expansion body 100 that is provided with a predetermined cutting unit 116.

In accordance with an exemplary embodiment, the expansion body 100 illustrated in FIG. 28 is provided with the cutting unit 116 disposed in the distal side standing portion 115b of the concave portion 115. For example, an incision Hc can be formed in the edge portion Hhe of the through-hole Hh as illustrated in FIG. 29 by moving the expansion body 100 to the proximal side (left side in the drawing) from a state where the distal side standing portion 115b is disposed on the distal side of the through-hole Hh (right side in the drawing) as illustrated in FIG. 28. The incision Hc formed by the cutting unit 116 is likely to cause no elastic biological tissue contraction, and thus the through-hole Hh can be maintained in the shape illustrated in FIG. 29.

Note that a cutter having a blade surface formed in a sharp shape, an electric knife, a laser cutter, or the like is capable of constituting the cutting unit 116. In addition, the cutting unit 116 can be provided in one expansion body 100 in combination with, for example, the maintenance treatment element 109 described above. In addition, the cutting unit 116 can be disposed in, for example, the proximal side standing portion 115c of the concave portion 115. In the case of such a configuration, the incision Hc in the edge portion Hhe of the through-hole Hh can be formed, for example, by moving the expansion body 100 to the distal side.

Figure 30:
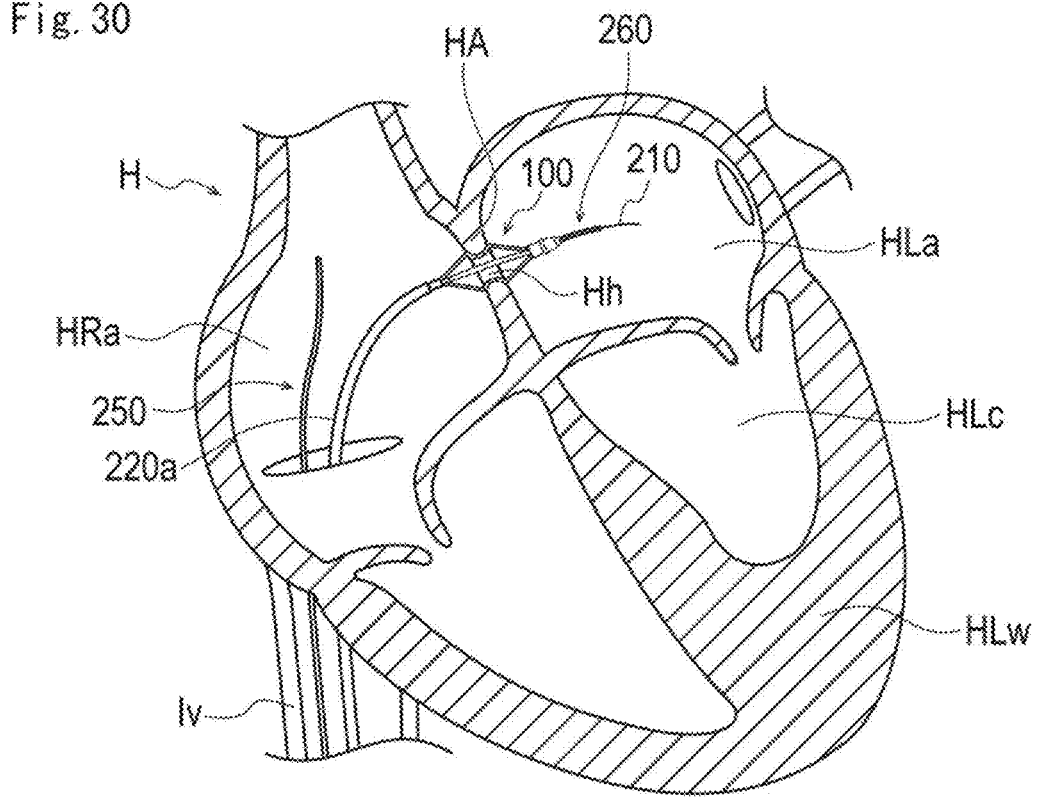
FIG. 30 is a cross-sectional view schematically illustrating an example of the process of confirming the hemodynamics in the vicinity of the through-hole formed in the atrial septum.

A modification example of the hemodynamic confirmation process is illustrated in FIG. 30.

Although an example in which the hemodynamic confirmation in the vicinity of the through-hole Hh is performed by means of the hemodynamic confirmation device 240 (such as an echo catheter) disposed in the right atrium HRa has been described in the embodiment described above, the hemodynamic confirmation can be performed by means of, for example, pressure measurement catheters 250 and 260. Specifically, as illustrated in FIG. 30, the pressure measurement catheter 250 is delivered to the right atrium HRa via the inferior vena cava Iv and the pressure measurement catheter 260 is delivered to the left atrium HLa via the inferior vena cava Iv, the right atrium HRa, and the through-hole Hh. A surgeon acquires the pressure (blood pressure) of the right atrium HRa by using the pressure measurement catheter 250, acquires the pressure (blood pressure) of the left atrium HLa by using the pressure measurement catheter 260, and causes a monitor or the like to display the acquired pressures. The surgeon can confirm the pressure difference between the right atrium HRa and the left atrium HLa based on the display content of the monitor and can grasp the hemodynamics.

A known catheter device can be appropriately used for the pressure measurement catheters 250 and 260. In addition, the pressure measurement catheter 250 delivered to the left atrium HLa can be delivered via, for example, the guide wire lumen 159 of the medical device 10 (see FIG. 3). In accordance with an exemplary embodiment, the hemodynamic confirmation can be performed, for example, by inserting an echo catheter into the esophagus and acquiring an echo image of the heart H from the esophagus side.

Next, an example of an expansion body that expands the through-hole Hh will be described.

The expansion bodies described below have a function of expanding the through-hole Hh and a function of not suppressing the blood flow through the through-hole Hh in a state of being disposed in the through-hole Hh. Accordingly, by using each of the expansion bodies described below, the hemodynamics in the vicinity of the through-hole Hh with the expansion body inserted in the through-hole Hh can be confirmed.

Figure 31:
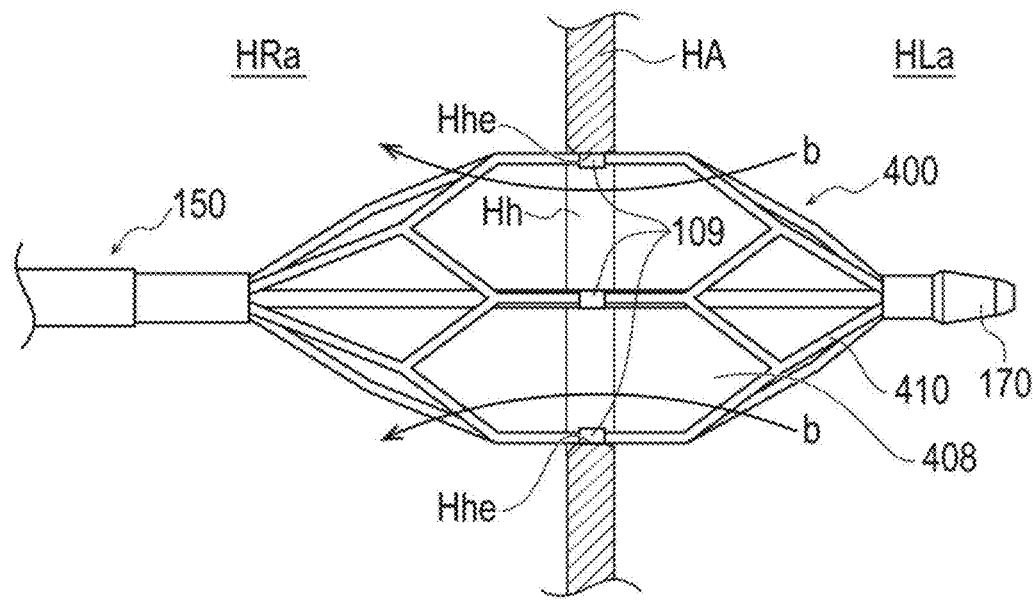
FIG. 31 is a cross-sectional view schematically illustrating an example of the expansion body.

An expansion body 400 illustrated in FIG. 31 includes an expandable skeleton (strut) 410 and a circulation portion 408 including a gap formed in the skeleton 410. The expansion body 400 can be manufactured, for example, by a notch that has a predetermined pattern being formed in a metallic pipe material.

Figure 32:
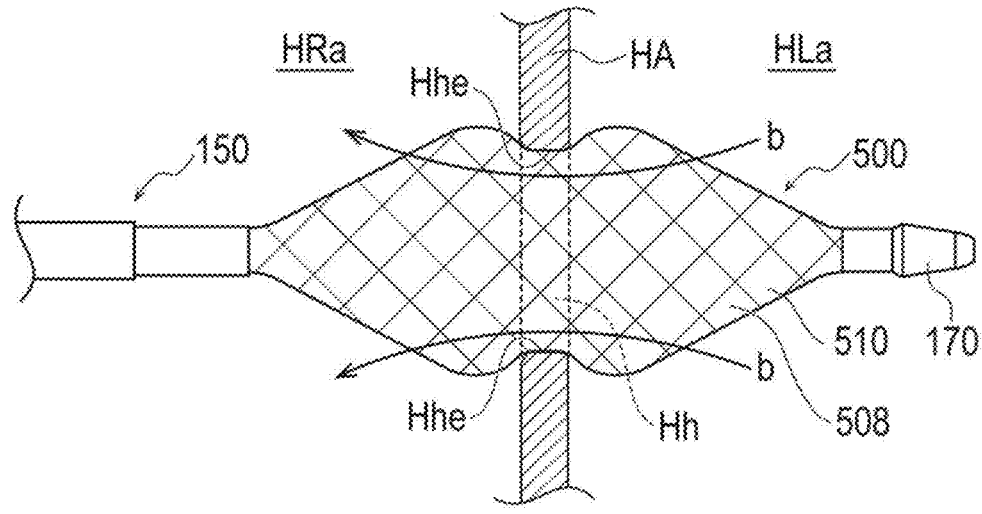
FIG. 32 is a cross-sectional view schematically illustrating an example of the expansion body.

An expansion body 500 illustrated in FIG. 32 includes a main body portion 510 including a plurality of wires and a circulation portion 508 including a hole portion allowing the inside and the outside of the main body portion 510 to communicate with each other.

Figure 33:
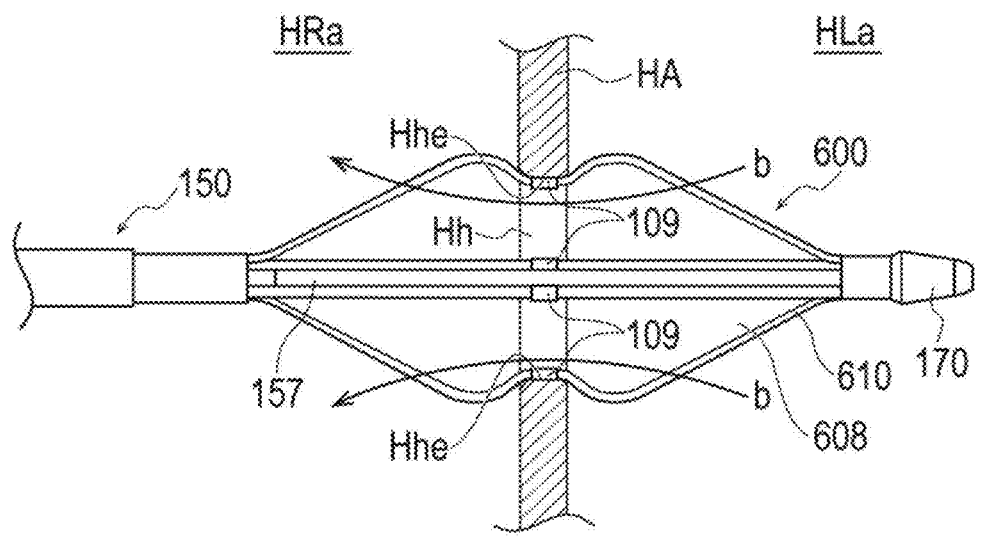
FIG. 33 is a cross-sectional view schematically illustrating an example of the expansion body.

An expansion body 600 illustrated in FIG. 33 includes a main body portion 610 including a plate-shaped member (such as a flat plate-shaped member) and a circulation portion 608 including a gap formed in the main body portion 610.

Figure 34:
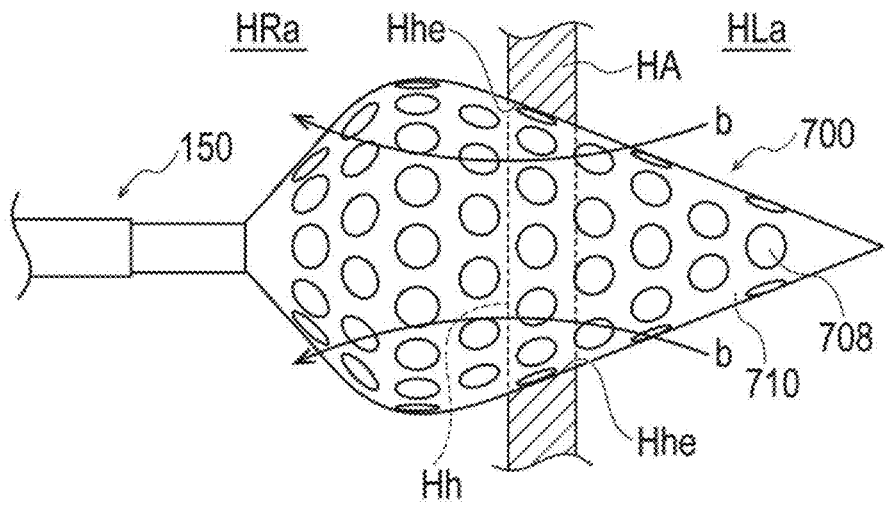
FIG. 34 is a cross-sectional view schematically illustrating an example of the expansion body.

An expansion body 700 illustrated in FIG. 34 includes a main body portion 710 including a plate-shaped member and a circulation portion 708 including a hole portion formed in the main body portion 710. The distal portion (right side in FIG. 34) of the main body portion 710 is formed in a tapered shape that tapers toward the distal side.

Figure 35:
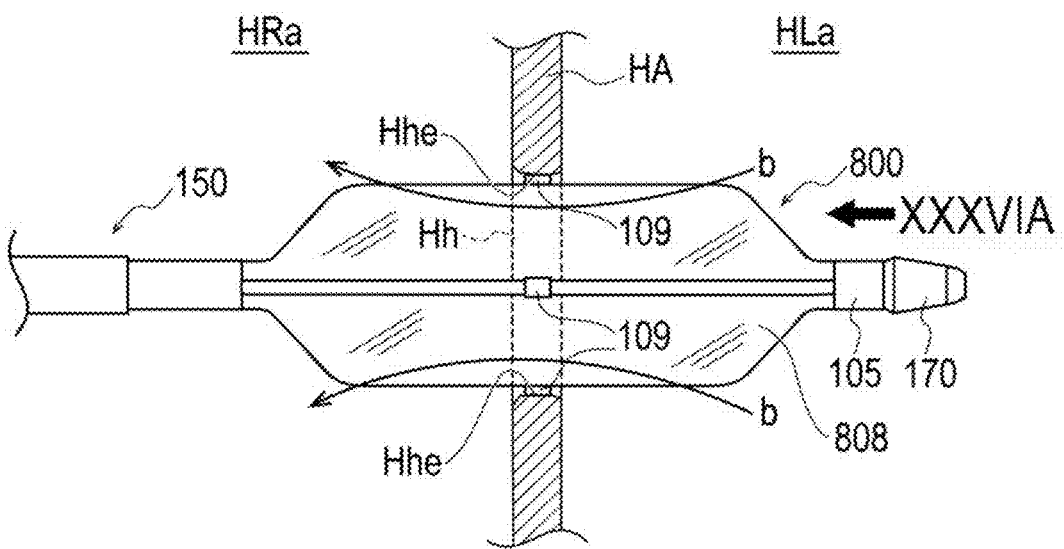
FIG. 35 is a cross-sectional view schematically illustrating an example of the expansion body.
Figure 36:
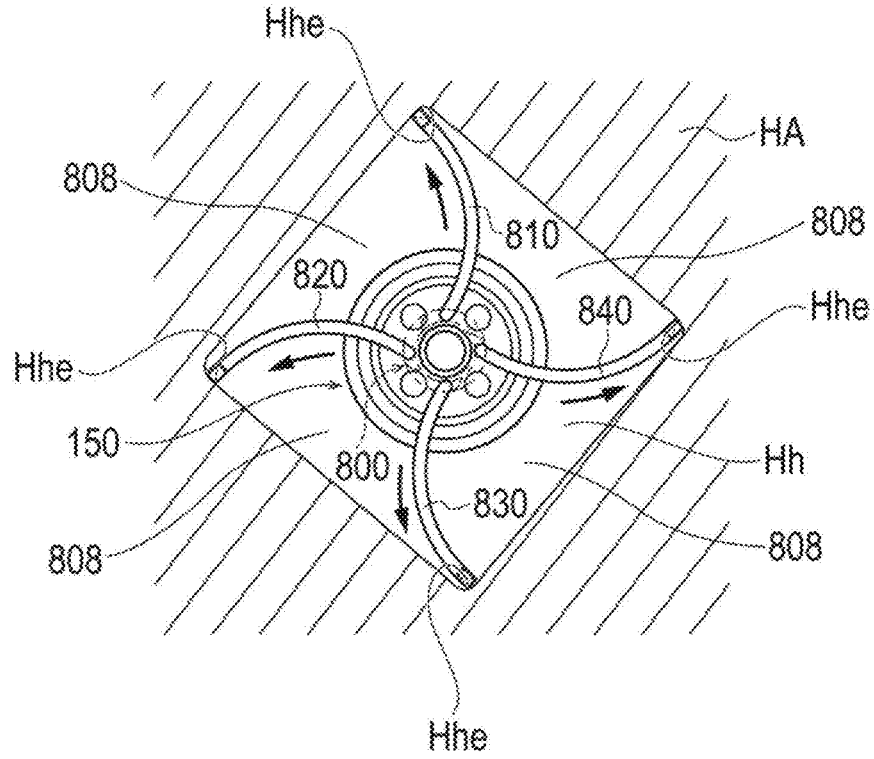
FIG. 36 is a front view of the through-hole viewed from the arrow XXXVIA direction illustrated in FIG. 35.

An expansion body 800 illustrated in FIGS. 35 and 36 includes a plurality of expansion portions 810, 820, 830, and 840 formed of plate-shaped members. The expansion body 800 that is contracted is disposed such that each of the expansion portions 810, 820, 830, and 840 is wound in the circumferential direction of the shaft portion 150 (state indicated by a broken line in FIG. 36). Gaps that form circulation portions 808 between the expansion portions 810, 820, 830, and 840 are formed when the expansion body 800 is expanded.

Figure 37:
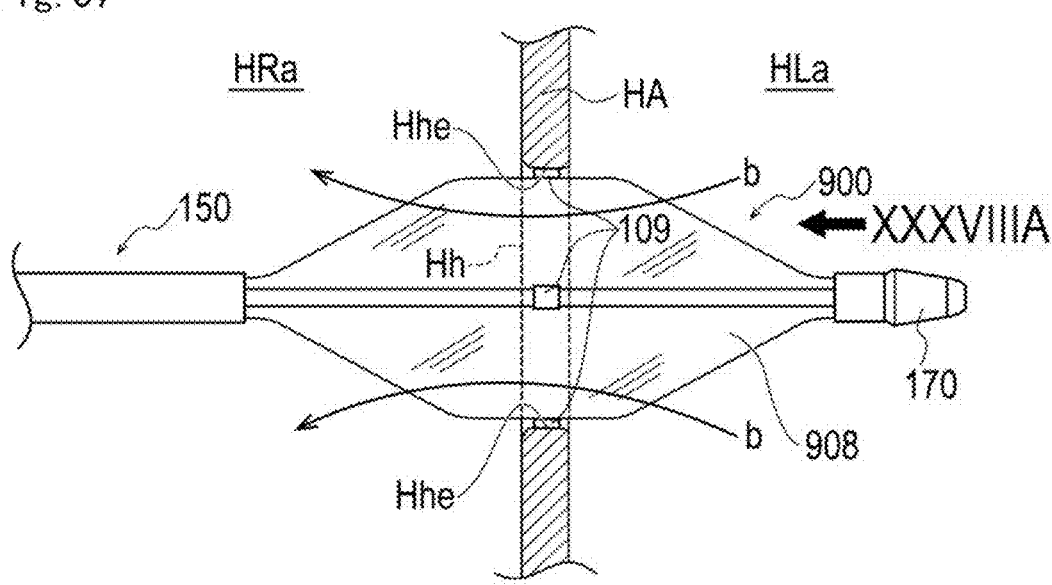
FIG. 37 is a cross-sectional view schematically illustrating an example of the expansion body.
Figure 38:
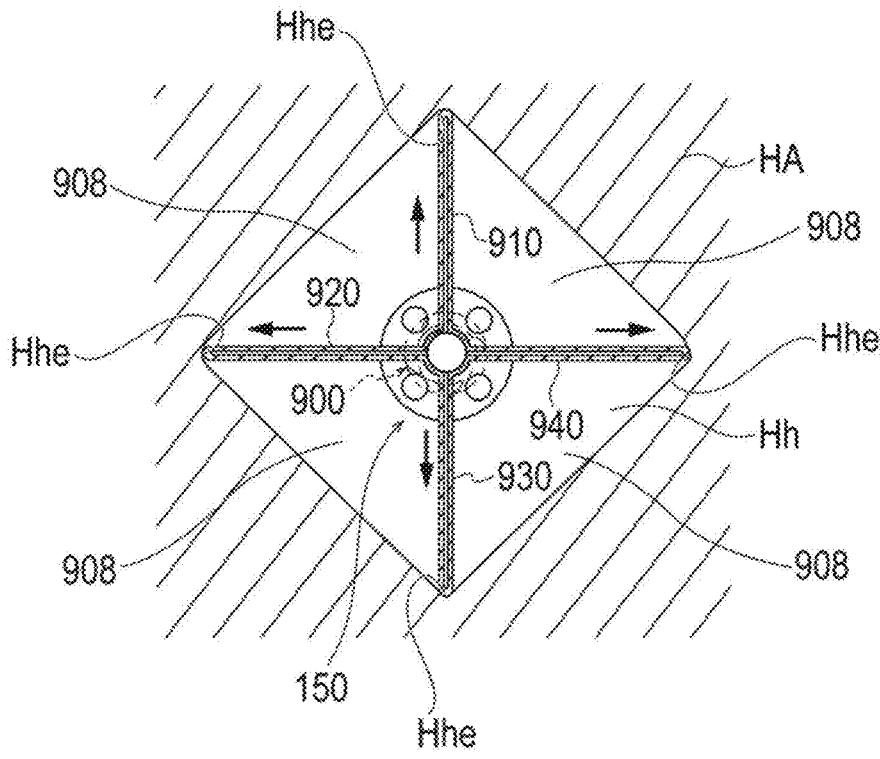
FIG. 38 is a front view of the through-hole viewed from the arrow XXXVIIIA direction illustrated in FIG. 37.

An expansion body 900 illustrated in FIGS. 37 and 38 includes a plurality of expansion portions 910, 920, 930, and 940 including balloons. The expansion body 900 that is contracted is disposed such that each of the expansion portions 910, 920, 930, and 940 is wound in the circumferential direction of the shaft portion 150 (state indicated by a broken line in FIG. 38). Each of the expansion portions 910, 920, 930, and 940 is expanded as illustrated in FIG. 38 and the through-hole Hh can be widened when, for example, a fluid is supplied to the expansion body 900 via the shaft portion 150. In addition, gaps that form circulation portions 908 between the expansion portions 910, 920, 930, and 940 can be formed when the expansion body 900 is expanded. Note that the specific shape and the like of the expansion portion (balloon) 900 are not particularly limited to the illustration.

As described above, the expansion body that is used for the expansion of the through-hole Hh is not particularly limited in terms of shape, material, specific structure, and so on insofar as the expansion body can be inserted into the through-hole Hh and does not hinder the blood flow through the through-hole Hh. For example, the expansion body can be expanded by fluid supply insofar as the balloon structure illustrated in FIG. 37 is used. In addition, in a case where the expansion body is configured by means of a self-expanding material or the like as another structure, the expansion body can be expanded and contracted by expansion body exposure and protrusion from a sheath or the like. In another example, the expansion body can be configured to be detachable from a shaft portion or can be configured to be indwellable in a through-hole.

Although the medical device and the treatment method according to the disclosure have been described through the plurality of embodiment and modification examples as described above, the disclosure is not limited to the content described in the embodiment and can be appropriately changed based on the description of the claims.

For example, the applications of the medical device are not limited to heart failure treatment and the medical device can be applied to various procedures for the purpose of treatment by means of a maintenance treatment element. In addition, omission of an additional member described in the embodiment, addition of an additional member not particularly described, and the like can be appropriately performed.

In addition, one form of the treatment method may include at least the expansion process of expanding a through-hole formed in the atrial septum, the confirmation process of confirming the hemodynamics in the vicinity of the through-hole, and the process of performing the maintenance treatment in order to maintain the size of the through-hole. In addition, another form of the treatment method may include at least the first expansion process of expanding a through-hole formed in the atrial septum, the second expansion process of expanding the through-hole more than in the first expansion process, and the process of performing the maintenance treatment with respect to the through-hole after the second expansion process.

In addition, each of the treatment methods described above can be widely applied to heart failure that develops with an increase in blood pressure on the left atrium side, heart failure that develops with an increase in blood pressure on the right atrium side, and general heart failure symptoms (including symptoms other than diastolic dysfunction).

The detailed description above describes embodiments of a medical device provided with a maintenance treatment element imparting energy to biological tissue and a treatment method performed on a heart failure patient. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A treatment method, the method comprising:
expanding a through-hole formed in an atrial septum so as to allow a right atrium and a left atrium of a heart failure patient to communicate with each other;
confirming hemodynamics of blood flow in a vicinity of the through-hole; and
performing maintenance treatment for maintaining a size of the through-hole with a medical device comprising a shaft portion, an expandable and contractible expansion body disposed distal of the shaft portion, the expansion body including a plurality of linear expansion portions disposed at different positions in a circumferential direction of the shaft portion, each of the plurality of linear expansion portions including a concave portion recessed in a direction intersecting with an axial direction of the shaft portion, and a maintenance treatment element disposed in each of the linear expansion portions.

2. The method according to claim 1, further comprising:
confirming the hemodynamics of the blood flow through the through-hole formed in the atrial septum of the heart failure patient when the concave portion of the medical device is disposed in the through-hole; and performing the maintenance treatment of the through-hole while biological tissue is in the concave portion.

3. The method according to claim 1, wherein the concave portion of each of the plurality of linear expansion portions includes a bottom portion, a distal side standing portion that is formed distal of the bottom portion in the axial direction and that rises in a direction intersecting with the axial direction from the bottom portion; and a proximal side standing portion that is formed proximal of the bottom portion and that rises in a direction intersecting with the axial direction from the bottom portion, the method comprising:

disposing the maintenance treatment element in at least one of the bottom portion and the distal side standing portion.

4. The method according to claim 3, comprising:

forming the distal side standing portion and the proximal side standing portion having substantially a same height dimension in a direction intersecting with the axial direction; and disposing the maintenance treatment element in the bottom portion.

5. The method according to claim 3, comprising:

forming the distal side standing portion to be larger than the proximal side standing portion in height dimension in a direction intersecting with the axial direction; and disposing the maintenance treatment element in the distal side standing portion.

6. A treatment method, the method comprising:

expanding a through-hole formed in an atrial septum in a first expansion process to allow a right atrium and a left atrium of a heart failure patient to communicate with each other;

expanding the through-hole more than in the first expansion process in a second expansion process; and performing maintenance treatment for maintaining the through-hole with respect to the through-hole after the second expansion process with a medical device comprising a shaft portion, an expandable and contractible expansion body disposed distal of the shaft portion, the expansion body including a plurality of linear expansion portions disposed at different positions in a circumferential direction of the shaft portion, each of the plurality of linear expansion portions including a concave portion recessed in a direction intersecting with an axial direction of the shaft portion, and a maintenance treatment element disposed in each of the linear expansion portions.

7. The method according to claim 6, comprising:

performing the first expansion process and the second expansion process with the concave portion of the medical device in the through-hole.

\* \* \* \* \*